(12) United States Patent
Kemp

(10) Patent No.: US 9,709,379 B2
(45) Date of Patent: Jul. 18, 2017

(54) OPTICAL COHERENCE TOMOGRAPHY SYSTEM THAT IS RECONFIGURABLE BETWEEN DIFFERENT IMAGING MODES

(71) Applicant: VOLCANO CORPORATION, San Diego, CA (US)

(72) Inventor: Nathaniel J. Kemp, Concord, MA (US)

(73) Assignee: Volcano Corporation, San Diego, CA (US)

( * ) Notice: Subject to any disclaimer, the term of this patent is extended or adjusted under 35 U.S.C. 154(b) by 82 days.

(21) Appl. No.: 14/107,439

(22) Filed: Dec. 16, 2013

(65) Prior Publication Data

US 2014/0176963 A1    Jun. 26, 2014

Related U.S. Application Data

(60) Provisional application No. 61/740,104, filed on Dec. 20, 2012.

(51) Int. Cl.
*G01B 11/02* (2006.01)
*G01B 9/02* (2006.01)
*A61B 5/00* (2006.01)

(52) U.S. Cl.
CPC ........ *G01B 9/02091* (2013.01); *A61B 5/0066* (2013.01); *G01B 9/0203* (2013.01); *G01B 9/02004* (2013.01); *G01B 9/02009* (2013.01); *G01B 9/02048* (2013.01); *G01B 9/02069* (2013.01); *A61B 5/7225* (2013.01)

(58) Field of Classification Search
CPC ............ G01B 9/02091; G01B 9/02004; G01B 9/02009; G01B 9/0203; G01B 9/02048; G01B 9/02069; A61B 5/0066; A61B 5/7225

USPC .................................................. 356/479, 497
See application file for complete search history.

(56) References Cited

U.S. PATENT DOCUMENTS

| | | |
|---|---|---|
| 3,301,258 A | 1/1967 | Werner |
| 3,617,880 A | 11/1971 | Cormack et al. |
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |

(Continued)

FOREIGN PATENT DOCUMENTS

| | | |
|---|---|---|
| EP | 1041373 A2 | 10/2000 |
| EP | 01172637 A1 | 1/2002 |

(Continued)

OTHER PUBLICATIONS

Sihan et al., 2008, A novel approach to quantitative analysis of intraluminal optical coherence tomography imaging, Comput. Cardiol:1089-1092.

(Continued)

*Primary Examiner* — Tarifur Chowdhury
*Assistant Examiner* — Jonathon Cook

(57) ABSTRACT

The invention generally relates to an optical coherence tomography system that is reconfigurable between two different imaging modes and methods of use thereof.

6 Claims, 14 Drawing Sheets

(56) References Cited

U.S. PATENT DOCUMENTS

| | | |
|---|---|---|
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |

(56) References Cited

U.S. PATENT DOCUMENTS

| | | |
|---|---|---|
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,943,352 A * | 8/1999 | Fee ............ H01S 5/0687 372/108 |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B1 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |

(56) References Cited

U.S. PATENT DOCUMENTS

| | | |
|---|---|---|
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |

(56) References Cited

U.S. PATENT DOCUMENTS

| | | |
|---|---|---|
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0216621 A1 | 11/2003 | Alpert |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |

(56) References Cited

U.S. PATENT DOCUMENTS

| | | |
|---|---|---|
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childlers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |

(56) References Cited

U.S. PATENT DOCUMENTS

| | | |
|---|---|---|
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1* | 2/2009 | Kemp ............... A61B 5/0066 356/479 |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0110376 A1 | 5/2010 | Everett |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |

(56) References Cited

U.S. PATENT DOCUMENTS

| | | |
|---|---|---|
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0271772 A1* | 10/2013 | Johnson et al. ............... 356/479 |
| 2013/0296704 A1 | 11/2013 | Magnin et al. |
| 2013/0303907 A1 | 11/2013 | Corl |
| 2013/0303920 A1 | 11/2013 | Corl |
| 2013/0308136 A1* | 11/2013 | Kuznetsov et al. .......... 356/479 |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/44296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/006886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

(56) References Cited

FOREIGN PATENT DOCUMENTS

OTHER PUBLICATIONS

Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vase. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells, EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt, 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12(24):6033-6039.
Zitova et al., 2003, Image registration methods: A survey. Image and Vision Computing, 21(11):977-1000.
International Search Report and Written Opinion mailed Nov. 2, 2012, for International Patent Application No. PCT/US12/53168, filed Aug. 30, 2013 (8 pages).
International Search Report and Written Opinion mailed on Apr. 14, 2014, for International Patent Application No. PCT/US2013/076148, filed Dec. 18, 2013 (8 pages).
International Search Report and Written Opinion mailed on Apr. 21, 2014, for International Patent Application No. PCT/US2013/076015, filed Dec. 18, 2013 (7 pages).
International Search Report and Written Opinion mailed on Apr. 23, 2014, for International Patent Application No. PCT/US2013/075328, filed Dec. 16, 2013 (8 pages).
International Search Report and Written Opinion mailed on Apr. 29, 2014, for International Patent Application No. PCT/US13/76093, filed Dec. 18, 2013 (6 pages).
International Search Report and Written Opinion mailed on Apr. 9, 2014, for International Patent Application No. PCT/US13/75089, filed Dec. 13, 2013 (7 pages).
International Search Report and Written Opinion mailed on Feb. 21, 2014, for International Patent Application No. PCT/US13/76053, filed Dec. 18, 2013 (9 pages).
International Search Report and Written Opinion mailed on Feb. 21, 2014, for International Patent Application No. PCT/US2013/076965, filed Dec. 20, 2013 (6 pages).
International Search Report and Written Opinion mailed on Feb. 27, 2014, for International Patent Application No. PCT/US13/75416, filed Dec. 16, 2013 (7 pages).
International Search Report and Written Opinion mailed on Feb. 28, 2014, for International Patent Application No. PCT/US13/75653, filed Dec. 17, 2013 (7 pages).

(56) References Cited

OTHER PUBLICATIONS

International Search Report and Written Opinion mailed on Feb. 28, 2014, for International Patent Application No. PCT/US13/75990, filed Dec. 18, 2013 (7 pages).
International Search Report and Written Opinion mailed on Jan. 16, 2009, for International Patent Application No. PCT/US08/78963 filed on Oct. 6, 2008 (7 Pages).
International Search Report and Written Opinion mailed on Jul. 30, 2014, for International Patent Application No. PCT/US14/21659, filed Mar. 7, 2014 (15 pages).
International Search Report and Written Opinion mailed on Mar. 10, 2014, for International Patent Application No. PCT/US2013/076212, filed Dec. 18, 2013 (8 pages).
International Search Report and Written Opinion mailed on Mar. 11, 2014, for International Patent Application No. PCT/US13/76173, filed Dec. 16, 2013 (9 pages).
International Search Report and Written Opinion mailed on Mar. 11, 2014, for International Patent Application No. PCT/US13/76449, filed Dec. 19, 2013 (9 pages).
International Search Report and Written Opinion mailed on Mar. 18, 2014, for International Patent Application No. PCT/US2013/076502, filed Dec. 19, 2013 (7 pages).
International Search Report and Written Opinion mailed on Mar. 18, 2014, for International Patent Application No. PCT/US2013/076788, filed Dec. 20, 2013 (7 pages).
International Search Report and Written Opinion mailed on Mar. 19, 2014, for International Patent Application No. PCT/US13/75349, filed Dec. 16, 2013 (10 pages).
International Search Report and Written Opinion mailed on Mar. 19, 2014, for International Patent Application No. PCT/US2013/076587, filed Dec. 19, 2013 (10 pages).
International Search Report and Written Opinion mailed on Mar. 19, 2014, for International Patent Application No. PCT/US2013/076909, filed Dec. 20, 2013 (7 pages).
International Search Report and Written Opinion mailed on Mar. 7, 2014, for International Patent Application No. PCT/US2013/076304, filed Dec. 18, 2013 (9 pages).
International Search Report and Written Opinion mailed on Mar. 7, 2014, for International Patent Application No. PCT/US2013/076480, filed Dec. 19, 2013 (8 pages).
International Search Report and Written Opinion mailed on Mar. 7, 2014, for International Patent Application No. PCT/US2013/076512, filed Dec. 19, 2013 (8 pages).
International Search Report and Written Opinion mailed on Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.

(56) References Cited

OTHER PUBLICATIONS

Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring—the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radio-frequency ablation lesion formation using an optical coherence tomography forward-imaging catheter, Journal of Biomedical Optics 15 (3):030516-1 (3 pages).

Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion mailed Mar. 11, 2014, for International Patent Application No. PCT/US13/75675, filed Dec. 17, 2013 (7 pages).
International Search Report and Written Opinion mailed Mar. 19, 2014, for International Patent Application No. PCT/US13/075353, filed Dec. 16, 2013 (8 pages).
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Machine translation of JP 2000-097846.
Machine translation of JP 2000-321034.
Machine translation of JP 2000-329534.
Machine translation of JP 2004-004080.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.

(56) References Cited

OTHER PUBLICATIONS

Morrison et al., 1984, Chimeric human antibody molecules: mouse antigen-binding domains with human constant region domains, PNAS 81:6851-6855.

Munson et al., 1980, Ligand: a versatile computerized approach for characterization of ligand-binding systems, Analytical Biochemistry, 107:220-239.

Nezam, 2008, High Speed Polygon-Scanner-Based Wavelength-Swept Laser Source in the Telescope-Less Configurations with Application in Optical Coherence Tomography, Optics Letters 33(15):1741-1743.

Nissen, 2001, Coronary Angiography and Intravascular Ultrasound, American Journal of Cardiology, 87 (suppl):15A-20A.

Nitenberg et al., 1995, Coronary vascular reserve in humans: a critical review of methods of evaluation and of interpretation of the results, Eur Heart J. 16(Suppl 1):7-21.

Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).

Nygren, 1982, Conjugation of horseradish peroxidase to Fab fragments with different homobifunctional and heterobifunctional cross-linking reagents. A comparative study, J. Histochem. and Cytochem. 30:407-412.

Oesterle et al., 1986, Angioplasty at coronary bifurcations: single-guide, two-wire technique, Cathet Cardiovasc Diagn., 12:57-63.

Okuno et al., 2003, Recent Advances in Optical Switches Using Silica-based PLC Technology, NTT Technical Review 1(7):20-30.

Oldenburg et al., 1998, Nanoengineering of Optical Resonances, Chemical Physics Letters 288:243-247.

Oldenburg et al., 2003, Fast-Fourier-Domain Delay Line for In Vivo Optical Coherence Tomography with a Polygonal Scanner, Applied Optics, 42(22):4606-4611.

Othonos, 1997, Fiber Bragg gratings, Review of Scientific Instruments 68(12):4309-4341.

Owens et al., 2007, A Survey of General-Purpose Computation on Graphics Hardware, Computer Graphics Forum 26(1):80-113.

Pain et al., 1981, Preparation of protein A-peroxidase mono conjugate using a heterobifunctional reagent, and its use in enzyme immunoassays, J Immunol Methods, 40:219-30.

Park et al., 2005, Real-time fiber-based multi-functional spectral-domain optical coherence tomography at 1.3 um., Optics Express 13(11):3931-3944.

Pasquesi et al., 2006, In vivo detection of exercise induced ultrastructural changes in genetically-altered murine skeletal muscle using polarization-sensitive optical coherence tomography, Optics Express 14(4):1547-1556.

Pepe et al., 2004, Limitations of the odds ratio in gauging the performance of a diagnostic, prognostic, or screening marker, American Journal of Epidemiology 159(9):882-890.

Persson et al., 1985, Acoustic impedance matching of medical ultrasound transducers, Ultrasonics, 23(2):83-89.

Placht et al., 2012, Fast time-of-flight camera based surface registration for radiotherapy patient positioning, Medical Physics 39(1):4-17.

Rabbani et al., 1999, Review: Strategies to achieve coronary arterial plaque stabilization, Cardiovascular Research 41:402-417.

Radvany et al., 2008, Plaque Excision in Management of Lower Extremity Peripheral Arterial Disease with the SilverHawk Atherectomy Catheter, Seminars in Interventional Radiology, 25(1):11-19.

Reddy et al., 1996, An FFT-Based Technique for Translation, Rotation, and Scale-Invariant Image Registration, IEEE Transaction on Image Processing 5(8):1266-1271.

Riechmann et al., 1988, Reshaping human antibodies for therapy, Nature, 332:323-327.

Rivers et al., 1992, Correction of steal syndrome secondary to hemodialysis access fistulas: a simplified quantitative technique, Surgery, 112(3):593-7.

Robbin et al., 2002, Hemodialysis Arteriovenous Fistula Maturity: US Evaluation, Radiology 225:59-64.

Rollins et al., 1998, In vivo video rate optical coherence tomography, Optics Express 3:219-229.

Sarunic et al., 2005, Instantaneous Complex Conjugate Resolved Spectral Domain and Swept-Source OCT Using 3×3 Fiber Couplers, Optics Express 13(3):957-967.

Satiani et al., 2009, Predicted Shortage of Vascular Surgeons in the United States, J. Vascular Surgery 50:946-952.

Schneider et al., 2006, T-banding: A technique for flow reduction of a hyper-functioning arteriovenous fistula, J Vasc Surg. 43(2):402-405.

Sen et al., 2012, Development and validation of a new adenosine-independent index of stenosis severity from coronary wave-intensity analysis, Journal of the American College of Cardiology 59(15):1392-1402.

Setta et al., 2005, Soft versus firm embryo transfer catheters for assisted reproduction: a systematic review and meta-analysis, Human Reproduction, 20(11):3114-3121.

Seward et al., 1996, Ultrasound Cardioscopy: Embarking on New Journey, Mayo Clinic Proceedings 71(7):629-635.

Shen et al., 2006, Eigengene-based linear discriminant model for tumor classification using gene expression microarray data, Bioinformatics 22(21):2635-2642.

\* cited by examiner

OPTICAL COHERENCE TOMOGRAPHY SYSTEM THAT IS RECONFIGURABLE BETWEEN DIFFERENT IMAGING MODES

CROSS-REFERENCE TO RELATED APPLICATIONS

This application claims the benefit of, and priority to, U.S. Provisional Application Ser. No. 61/740,104, filed Dec. 20, 2012, the contents of which are incorporated by reference herein in its entirety.

FIELD OF THE INVENTION

The invention generally relates to an optical coherence tomography system that is reconfigurable between different imaging modes and methods of use thereof.

BACKGROUND

Biomedical imaging technology is rapidly advancing. For example, magnetic resonance imaging (MRI), X-ray computed tomography, ultrasound, and confocal microscopy are all in widespread research and clinical use, and have resulted in fundamental and dramatic improvements in health care. However, there are many situations in which existing biomedical imaging technologies are not adequate. This is particularly true where high resolution (e.g. approximately 5-10 µm) imaging is required. In these situations, such imaging technology does not provide a physician with the required diagnostic information, and the physician must resort to other invasive examinations, such as biopsy and histopathologic examination, in order to obtain the required diagnostic information. Such examinations are potentially harmful, time consuming, and costly. Furthermore, there are many situations in which conventional excisional biopsy is not possible. Coronary artery disease, a leading cause of morbidity and mortality, is one important example of a disease in which conventional diagnostic excisional biopsy cannot be performed.

Development of depth-resolved light reflection or Optical Coherence Tomography (OCT) provides a high resolution imaging technique that addresses those concerns. OCT is an imaging technique that captures micrometer-resolution, three-dimensional images from within optical scattering media (e.g., biological tissue). OCT uses a narrow line width tunable laser source or a superluminescent diode source to emit light over a broad bandwidth to make in situ tomographic images with axial resolution of less than 10 µm and tissue penetration of 2-3 mm. OCT provides tissue morphology imagery at much higher resolution than other imaging modalities such as MRI or ultrasound. Further, with such high resolution, OCT can provide detailed images of a pathologic specimen without cutting or disturbing the tissue.

Typically, different parameters are required to image different types of vessels, e.g., coronary vessels versus peripheral vessels. Generally, coronary OCT imaging requires very high imaging rates to avoid ischemia during a lengthy blood clearance period and requires relatively moderate field of view to assess vessels with diameters up to approximately 6 mm. Alternatively, peripheral OCT imaging requires very large FOV to assess vessels with much larger diameters but can tolerate lower imaging rates because peripheral ischemia during blood clearance is not a big concern for patient safety. General technical limitations of OCT swept light sources (e.g. lasers) involve a tradeoff between coherence length and high sweep rates. Accordingly, separate OCT systems are used to image the different vessel types, one optimized for coronary imaging and a separate system optimized for peripheral imaging.

SUMMARY

The invention provides an optical coherence tomography (OCT) system that alternates between two imaging modes. A single OCT apparatus according to the invention is used for multiple imaging modes with automated reconfiguration of light source parameters and sample/clocking schemes for each mode. Preferably, one of the imaging modes is optimized for coronary imaging and the other imaging mode is optimized for peripheral imaging, however the invention is not limited to those two modes.

There are numerous different approaches for having a single OCT system that can switch between two different imaging modes. One way involves reconfiguration of the light source. Changing the sweep rate and coherence length of the light source allows for two different imaging modes. Generally, a first imaging mode uses a high sweep rate with a low coherence length. Such a configuration is acceptable for imaging a coronary vessel. A second imaging mode uses a low sweep rate with a high coherence. Such a configuration is acceptable for imaging a peripheral vessel.

Another way to have a single OCT system that can switch between two different imaging modes involves changing sampling characteristics of OCT signal digitization. That can involve changing an external K-space sample clock waveform, which may be accomplished either optically or electrically.

In other embodiments, the system includes two different image acquisition software modules, one for each imaging mode. Another approach is to have a system that is compatible with different types of catheters, one for each imaging mode.

The reconfigurable interferometer of the invention may be a stand-alone apparatus or may be combined with other imaging apparatuses. Other imaging systems, by way of example and not limitation, include spectroscopic devices, (including fluorescence, absorption, scattering, and Raman spectroscopies), intravascular ultrasound (IVUS), Forward-Looking IVUS (FLIVUS), high intensity focused ultrasound (HIFU), radiofrequency, optical light-based imaging, magnetic resonance, radiography, nuclear imaging, photoacoustic imaging, electrical impedance tomography, elastography, pressure sensing wires, intracardiac echocardiography (ICE), forward looking ICE and orthopedic, spinal imaging and neurological imaging, image guided therapeutic devices or therapeutic delivery devices, diagnostic delivery devices, and the like.

Other aspects of the invention provide methods for imaging an inside of a vessel. Those methods involve providing a reconfigurable optical coherence tomography (OCT) system, in which the OCT system is configured to alternate between two different imaging modes. Methods of the invention further involve configuring the OCT system to one of the two imaging modes. An imaging probe of the system is inserted into a vessel and used to image inside the vessel. The OCT system can be configured to the desired imaging mode before inserting the imaging probe into the vessel or after the imaging prove has been inserted into the vessel.

DETAILED DESCRIPTION

Figure 1:
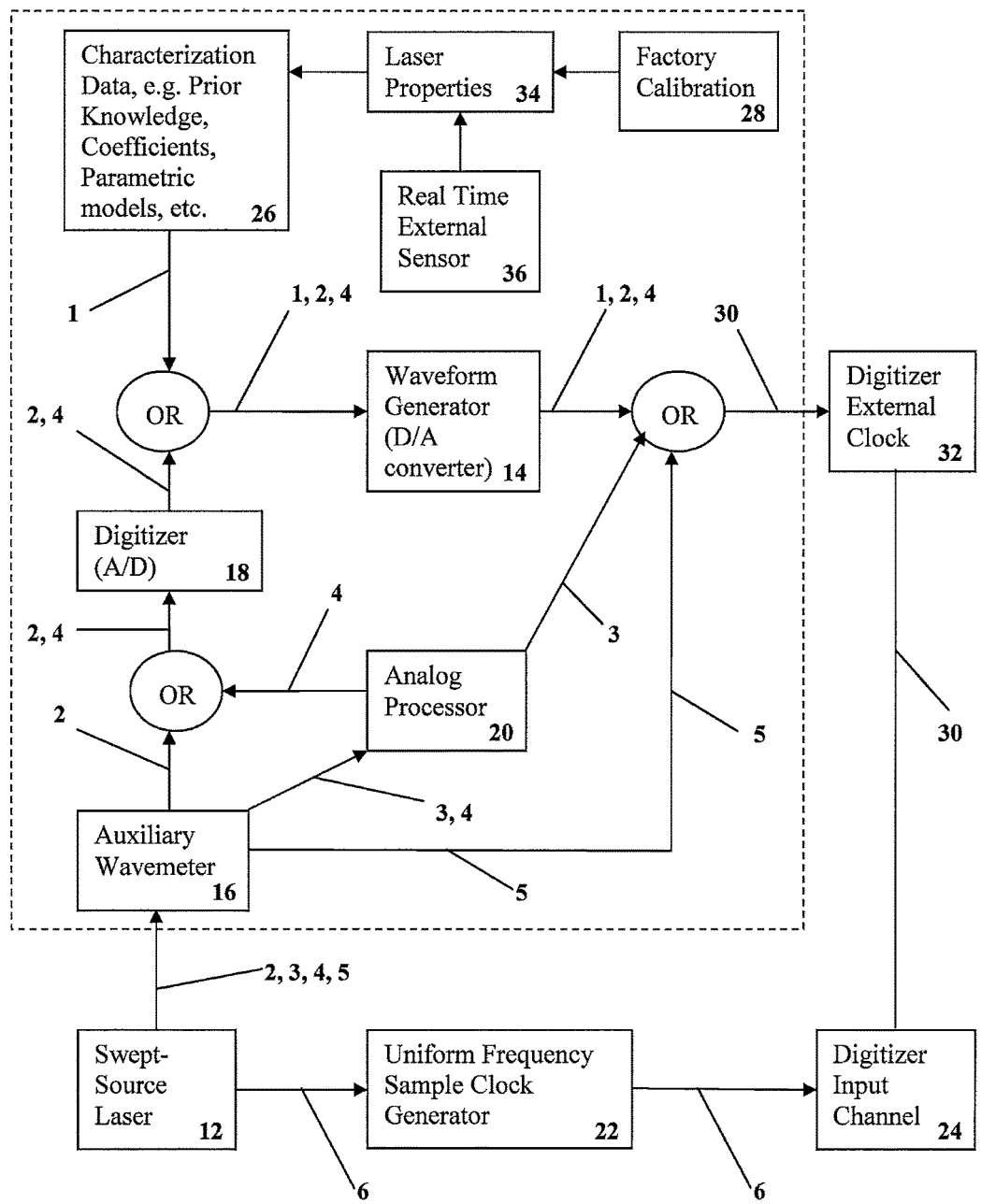
FIG. 1 is a schematic of the Uniform Frequency Sample Clock Pathways for the external clocking of a swept laser source.

Optical coherence tomography (OCT) is a medical imaging methodology using a miniaturized near infrared light-emitting probe. As an optical signal acquisition and processing method, it captures micrometer-resolution, three-dimensional images from within optical scattering media (e.g., biological tissue). An exemplary use of OCT is in interventional cardiology to help diagnose coronary artery disease. OCT allows the application of interferometric technology to see from inside, for example, blood vessels, visualizing the endothelium (inner wall) of blood vessels in living individuals.

OCT systems and methods are generally described in Castella et al. (U.S. Pat. No. 8,108,030), Milner et al. (U.S. Patent Application Publication No. 2011/0152771), Condit et al. (U.S. Patent Application Publication No. 2010/0220334), Castella et al. (U.S. Patent Application Publication No. 2009/0043191), Milner et al. (U.S. Patent Application Publication No. 2008/0291463), and Kemp, (U.S. Patent Application Publication No. 2008/0180683), the content of each of which is incorporated by reference in its entirety. Additional description of OCT systems and methods is described in Kemp (U.S. Pat. No. 8,049,900), Kemp (U.S. Pat. No. 7,929,148), Milner (U.S. Pat. No. 7,853,316), Feldman et al. (U.S. Pat. No. 7,711,413), Kemp et al., U.S. Patent Application Publication No. 2012/0224751), Milner et al. (U.S. Patent Application Publication No. 2012/0136259), Kemp et al., (U.S. Patent Application Publication No. 2012/0013914), Milner et al. (U.S. Patent Application Publication No. 2011/0152771), and Kemp et al. (U.S. Patent Application Publication No. 2009/0046295), the content of each of which is incorporated by reference in its entirety.

OCT systems of the invention include a light source. The light source may be any light source generally used with OCT. Exemplary light sources include a narrow line width tunable laser source or a superluminescent diode source. Examples of narrow line width tunable laser sources include, but are not limited to, lasers having a Bragg diffraction grating or a deformable membrane, lasers having a spectral dispersion component (e.g., a prism), or Fabry-Pérot based tuning laser.

OCT systems of the invention also include an interferometer. The interferometer may be any interferometer generally used with OCT. Typically, the interferometer will have a differential beam path for the light or a common beam path for the light. In either case, the interferometer is operably coupled to the light source. In a differential beam path layout, light from a broad band light source or tunable laser source is input into an interferometer with a portion of light directed to a sample and the other portion directed to a reference surface. A distal end of an optical fiber is interfaced with a catheter for interrogation of the target tissue during a catheterization procedure. The reflected light from the tissue is recombined with the signal from the reference surface forming interference fringes (measured by a photovoltaic detector) allowing precise depth-resolved imaging of the target tissue on a micron scale. Exemplary differential beam path interferometers are Mach-Zehnder interferometers and Michelson interferometers. Differential beam path interferometers are further described for example in Feldman et al. (U.S. Pat. No. 7,783,337) and Tearney et al. (U.S. Pat. Nos. 6,134,003 and 6,421,164), the content of each of which is incorporated by reference herein in its entirety.

The differential beam path optical layout of the interferometer includes a sample arm and a reference arm. The sample arm is configured to accommodate and couple to a catheter. The differential beam path optical layout also includes optical circulators to. The circulators facilitate transmission of the emitted light in a particular direction. Circulators and their use in OCT systems are further described for example in B. Bouma et al. (Optics Letters, 24:531-533, 1999), the entire disclosure of which is incorporated herein by reference. In the interferometer, there is a circulator where the emitted light is split to the sample arm and the reference arm. The system also includes a circulator that directs light to the sample and receives reflected light from the sample and directs it toward a detector. The system also includes a circulator that directs light to the reference surface and received reflected light from the reference surface and directs it toward the detector. There is also a circulator at the point at which reflected light from the sample and reflected light from the reference are recombined and directed to the detector.

In a common beam path system, rather than splitting a portion of the light to a reference arm, all of the produced light travels through a single optical fiber. Within the single fiber is a reflecting surface. A portion of the light is reflected off that surface prior to reaching a target tissue (reference)

and a remaining portion of the light passes through the reflecting surface and reaches the target tissue. The reflected light from the tissue recombines with the signal from the reference forming interference fringes allowing precise depth-resolved imaging of the target tissue on a micron scale. Common beam path interferometers are further described for example in Vakhtin, et al. (Applied Optics, 42(34):6953-6958, 2003), Wang et al. (U.S. Pat. No. 7,999, 938), Tearney et al. (U.S. Pat. No. 7,995,210), and Galle et al. (U.S. Pat. No. 7,787,127), the content of each of which is incorporated by reference herein in its entirety.

The common beam path optical layout of the interferometer includes a single array of optical fibers that are connected to a circulator. The array of optical fibers are configured to accommodate and couple to a catheter. The circulator directs light transmitted from the light source through the array of optical fibers of the common beam path optical layout to a sample and reference, and receives the reflected light from the sample and reference and directs it to the detector.

OCT systems of the invention include a detector. The detector includes photodetection electronics. The detector can support both balanced and non-balanced detection. OCT detectors are described for example in Kemp (U.S. Pat. No. 8,049,900), Kemp (U.S. Pat. No. 7,929,148), Milner (U.S. Pat. No. 7,853,316), Feldman et al. (U.S. Pat. No. 7,711, 413), Kemp et al., U.S. Patent Application Publication No. 2012/0224751), Milner et al. (U.S. Patent Application Publication No. 2012/0136259), Kemp et al., (U.S. Patent Application Publication No. 2012/0013914), Milner et al. (U.S. Patent Application Publication No. 2011/0152771), and Kemp et al. (U.S. Patent Application Publication No. 2009/0046295), the content of each of which is incorporated by reference in its entirety.

OCT systems of the invention may conduct any form of OCT known in the art. One manner for conducting OCT may be Swept-Source OCT ("SS-OCT"). SS-OCT time-encodes the wavenumber (or optical frequency) by rapidly tuning a narrowband light source over a broad optical bandwidth. The high speed tunable laser sources for SS-OCT exhibit a nonlinear or non-uniform wavenumber vs. time [k(t)] characteristic. As such, SS-OCT interferograms sampled uniformly in time [S(t), e.g., using an internal digitizer clock] must be remapped to S(k) before Fourier transforming into the path length (z) domain used to generate the OCT image. An SS-OCT system and methods for its use are described in Kemp et al., (U.S. Patent Application Publication No. 2012/ 0013914). The content of which is incorporated by reference herein in its entirety.

Generally speaking, a Uniform Frequency Sample Clocking 10 systems and methods for a swept laser source 12 are generally shown in FIG. 1. The Uniform Frequency Sample Clocking 10 comprises at least one Pathway, where some embodiments of the Pathways are generally shown as line arrows in FIG. 1. The line arrows represent electronic or optical coupling elements, such as wires, fibers, and the like. In one embodiment, Uniform Frequency Sample Clocking 10 includes Pathway 1 comprising characterizing 26 the swept laser source 12, creating a digital representation of the waveform based from the characterization data 26, and generating a clock signal 30 using a waveform generator 14 (i.e. a Digital-Analog ("D/A") converter) to output the clock signal 30 to a digitizer external clock 32. The Uniform Frequency Sample Clocking 10 may include Pathway 2 comprising coupling the swept laser source 12 to an auxiliary wavemeter 16, digitally processing the auxiliary wavemeter 16 output with an Analog-Digital ("A/D") digitizer 18, and processing the digitizer's 18 output on the D/A converter 14 to generate the clock signal 30 outputted to the digitizer external clock 32. The Uniform Frequency Sample Clocking 10 may include Pathway 3 comprising coupling the swept laser source 12 to the auxiliary wavemeter 16 and processing auxiliary wavemeter 16 output using an analog processor 20 to generate the clock signal 30. The Uniform Frequency Sample Clocking 10 may include Pathway 4 comprises coupling the swept laser source 12 to the auxiliary wavemeter 16, processing the auxiliary wavemeter 16 output with the analog processor 20, digitizing the analog processor's 20 output with the digitizer 18, digitally processing the auxiliary wavemeter 16 output with the D/A converter 19 to generate the clock signal 30. The Uniform Frequency Sample Clocking 10 may include Pathway 5 comprising coupling the swept laser source 12 to the auxiliary wavemeter 16 to directly generate a uniform-frequency sample clock signal with no pre-processing. The Uniform Frequency Sample Clocking 10 may include Pathway 6 coupling the swept laser source 12 to a Uniform Frequency Sample Clock Generator 22 outputting to a digitizer 24 to generate the clock signal 30. The Uniform Frequency Sample Clocking 10 systems and Pathways provide for external clocking of the swept laser source 12 and can provide a different clocking signal through independent Pathways, in combination and in any particular order, to generate the clock signal, process the clock signal, and transmit the clock signal to the digitizer for uniform sampling of detected light in the wavenumber domain. For each acquisition channel, one clock signal may be active at a given time, which may be switched between different clock signals in any particular combination or order. Alternatively, the Uniform Frequency Sample Clocking 10 Pathways may be combined with each other, in any sequence of combinations. More particularly, the Uniform Frequency Sample Clock Pathways 10 provide external clocking of detected light first emitted from the swept laser source for OCT systems. The term "Uniform Frequency Sample Clocking" and "linear sampling in the wavenumber domain" are equivalent terms, as used in the specification. The term "external clock signal" is specific to the type of signal applied to the external clock signal input or the clock signal input of the digitizer external clock 32. The term "clock signal" is the signal as applied to the AD converter card.

The swept laser source 12 includes emitted light with a mean frequency of the output spectrum that varies over time. The term "swept laser source" is synonymous with a "tunable laser source", i.e. tuning a laser source over a period of time at a certain frequency. The mean optical frequency of light emitted from the swept source may change continuously over time at a tuning speed that is greater than 100 terahertz per millisecond and repeatedly with a repetition period. range of sweep speeds for the table laser source— specifying a range of sweep speeds (e.g., 10,000-10,000,000 Sweeps/sec). The swept laser source 12 may be any tunable laser source that rapidly tunes a narrowband light emission through a broad optical bandwidth. The tuning range of the swept source may have a tuning range with a center wavelength between approximately 500 nanometers and 2000 nm, a tuning width of approximately greater than 1% of the center wavelength, and an instantaneous line width of less than approximately 10% of the tuning range. Alternatively, more than one optical source may be combined to produce the swept laser source, or a continuously swept multi-wavelength laser emitting several optical frequencies or wavelengths simultaneously. While tunable lasers and swept-source lasers are included as the swept laser source, Fourier Domain Mode Locking ("FDML") lasers may be included as the laser source. In FDML, the spectrum, rather than the amplitude of the field, is modulated. A dynamic spectral window function (wavelength window which changes in time), rather than a temporal one (time window with no wavelength dependence), is applied. As a result, the laser generates a sequence of narrowband optical frequency sweeps at the cavity repetition rate or a harmonic thereof. Multiple tunable wavelength sources may be included, where each tunable wavelength source has a receiver, so each tunable wavelength source is coupled with a detector. The composite of all the tunable wavelength laser sources and detectors can act as very large bandwidth laser source. This frequency-swept output can also be thought of as a sequence of highly chirped, long pulses, with a fixed phase relationship between successive frequency sweeps.

Figure 2:
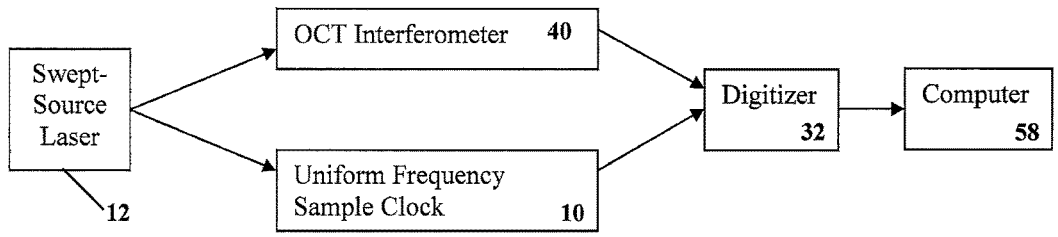
FIG. 2 is a schematic of one embodiment of the Uniform Frequency Sample Clock coupled with an OCT Interferometer.

In one embodiment, the swept laser source 12 provides the swept optical output to an OCT interferometer 40 and the Uniform Frequency Sample Clock 10, as shown in FIG. 2. Light emitted from the swept laser source 12 is split between the OCT interferometer 40 and the uniform frequency sample clock 10. The swept laser source 12 may be split in any desired ratio, including, but not limited to 95/5, 90/10, 85/15, 80/20, etc. to the OCT interferometer 40 and the Uniform Frequency Sample Clock 10, respectively. The Uniform Frequency Sample Clock 10 and the OCT interferometer 40 are then coupled to the digitizer 32 and then to a computer for processing and imaging.

Figure 15:
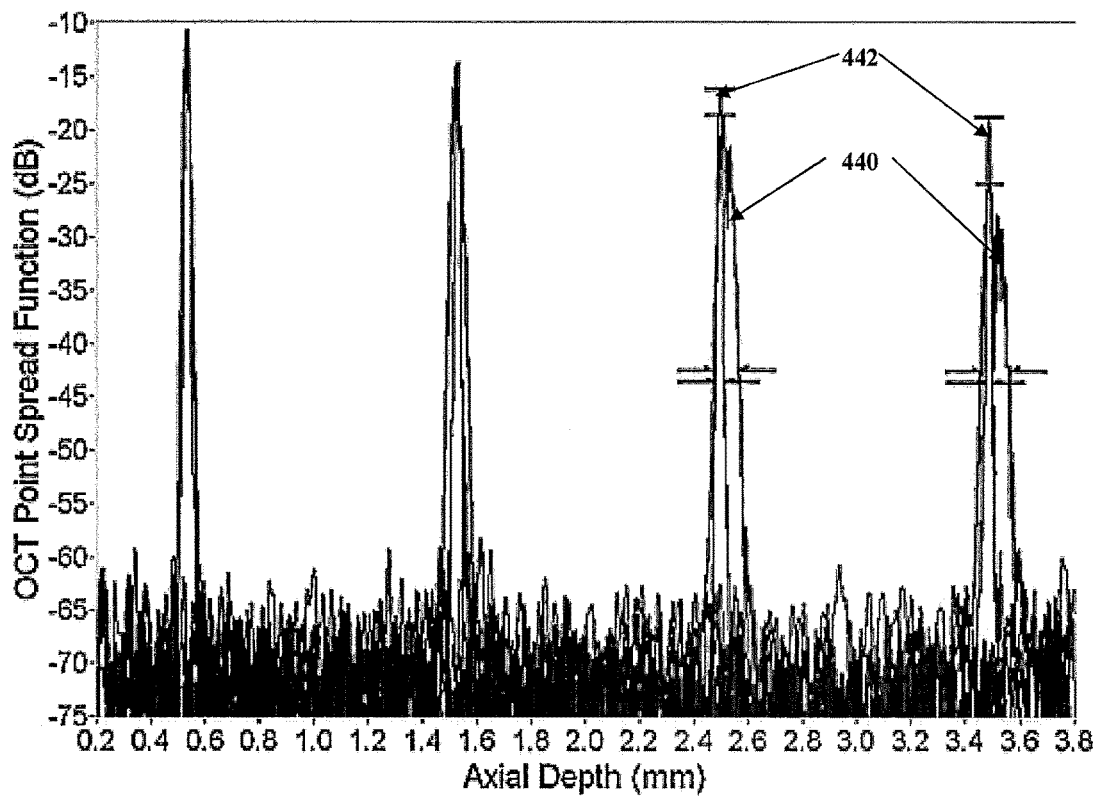
FIG. 15 is an OCT point spread functions vs. depth for an internally clocked/remapped scheme (440) and the externally clocked scheme 442

The OCT interferometer 40 splits the light emitted from the swept source to a reference surface and a sample arm, which recombines at the output of the interferometer. The OCT interferometer may take any of the variety of configurations known in the art, including, but not limited to, a Michelson interferometer, a Mach-Zehnder Interferometer, and/or a common path interferometer, etc. The Uniform Frequency Sampling clock generator 22 receives light from the swept source or the previously characterized swept source data and outputs to the digitizer to provide linear sampling in the wavenumber (k) or optical frequency (.nu.) domain, allowing direct Fourier transformation into the pathlength (z) domain for real time OCT imaging. The real-time OCT imaging comprises (1) Uniform Frequency Sampling; and (2) direct Fourier transformation of fringe data for real-time OCT imaging. Direct Fourier transformation requires a digital processing element that does the Fourier transform of the Uniform Frequency Sampled OCT fringe data or the "OCT signal data". Uniform Frequency Sampled OCT fringe data or the "OCT signal data" are used synonymously throughout. Generally speaking, the Uniform Frequency Sample clock 10 provides for linear sampling in the wavenumber domain, digitizing the OCT fringe data in the wavenumber domain for real-time OCT imaging, and combinations thereof. FIG. 15 compares axial point spread functions and OCT images generated with uniform time sampling vs. the uniform frequency sample clocking approach 10 using the Pathways discussed below.

Pathway 1: Characterizing the Swept Laser Source

In one embodiment, the Uniform Frequency Sample Clock 10 includes Pathway 1 comprising a step of characterizing light emitted by the swept laser source 12, creating a digital representation of the waveform based on the characterization data 26, and repeatedly outputting the characterization data 26 for each subsequent optical trigger that occurs as the laser is sweeping, as shown as Pathway 1 in FIG. 1. Data for characterizing light emitted from the swept laser source ("characterization data") is generated using a high-speed D/A converter, i.e. the waveform generator 14, which is then coupled to the digitizer's 32 external clock input port. The D/A converter 14 outputs the generated Uniform Frequency Sample Clock signal for each laser sweep, triggered by an electrical synchronization pulse or an optical trigger 54 derived from the swept-source laser output. There are several ways to generate the optical trigger 54. In one embodiment, the optical trigger 54 is generated from an optical trigger generator 60, discussed below. In another embodiment, the optical trigger 54 is derived from an optical tuning element in the swept laser source, as the signal may be generated actively or passively. When light is emitted from the swept laser source and interacts with an optical tuning element at the output of the swept laser source, the optical trigger signal is provided. The optical tuning element may be static and does not necessarily need to be actively tuned to function in the role providing the optical trigger signal. Another embodiment to generate the optical trigger 54 is to sample the light with an optical frequency selective element, i.e. a grating spectrometer, interference filter, Fabry-Perot filter, and the like, or combination there-of, and a photo-detector coupled to an A/D converter to provide the optical trigger. So there may be two different optical tuning elements, one within the laser source that functions to tune the laser and one that can be placed at the output of the tuning laser source, which can be used to provide a trigger signal. Combinations of these optical tuning element embodiments can be employed to generate an optimum optical trigger 54.

Figure 3:
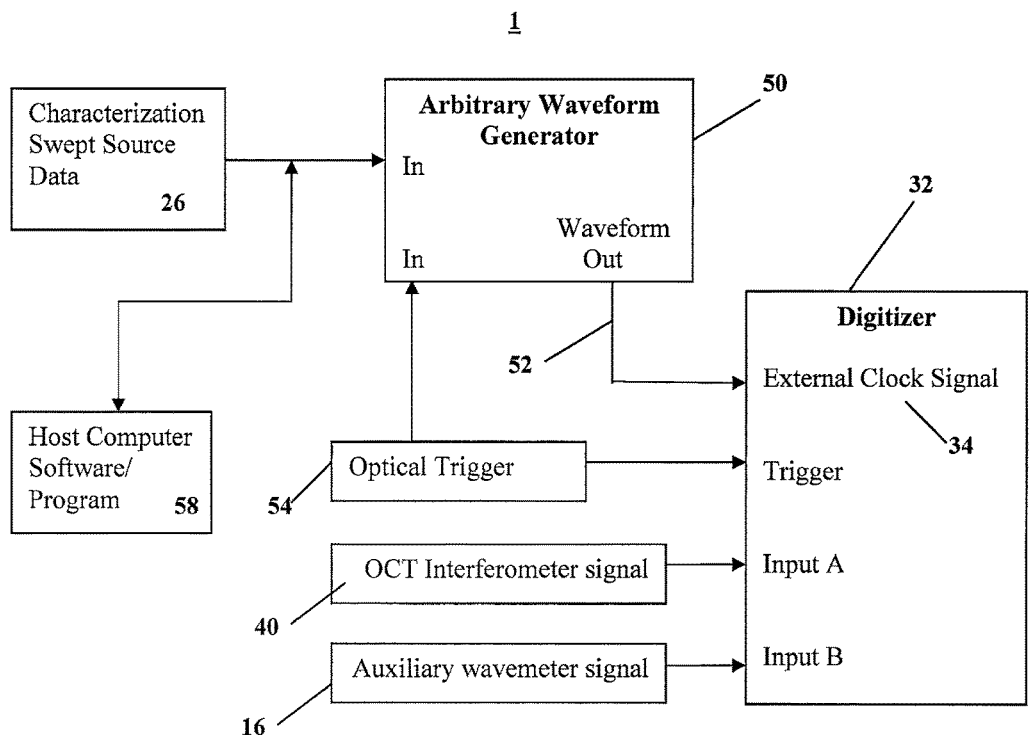
FIG. 3 is a schematic of one embodiment of Pathway 1.

In one embodiment, the D/A converter 14 may comprise an arbitrary waveform generator 50, as shown in FIG. 3. The arbitrary waveform generator 50 (CompuGen, Lockport, Ill.) provides aperiodic or periodic analog waveforms 52 as their output and generates a pre-programmed waveform every time a trigger event occurs. The pre-programmed waveform is stored in the on-board memory of the arbitrary waveform generator. Arbitrary waveforms 52 are generated by creating a digital representation of the waveform based on the characterization data 26 of light emitted from the swept laser source in the memory of the arbitrary waveform generator. The digital representation pattern is converted into an analog signal using a high-speed Digital-to-Analog converter and conditioning amplifiers (buffers and attenuators) within the arbitrary waveform generator 50. The external clock signal 34 is derived from the characterization data 26 of the swept source during a start-up calibration step, and then repeatedly outputted by the arbitrary waveform generator for each subsequent optical trigger 54 signal that occurs as the laser is sweeping. Alternatively, the external clock signal 34 from characterization data 26 can also be completed periodically according to some schedule programmed by a computer software 58, or may be performed in response to some event such as a parameter (or combination of parameters) of the source changing (e.g., temperature). The uniform frequency sample clock by the characterization of the swept laser source data 26 allows acquisition (analog to digital conversion) of OCT interferometer 40 data directly in wavenumber (k) space.

As shown in FIG. 1, characterizing the swept laser source data 26 may include a factory calibration 28 of the swept laser source; obtaining laser properties 34 of the laser source; or obtaining a parametric model of the swept laser source. The factory calibration 28 of the swept laser source may be obtained from the manufacturer of the swept laser source. Obtaining laser properties 34 of the laser source comprises a real time external sensor to obtain optical and environmental data about the swept laser source, such as temperature, position of optical elements, gradient, etc. The characterization data 26 may include prior knowledge about the swept laser source in the form of coefficients, a look-up table, or the parametric model to generate the clock signal. A lookup table (LUT) is a data structure, usually an array or associative array, used to replace a runtime computation with a simpler array indexing operation. The speed gain can be significant, since retrieving a value from memory is often faster than undergoing an expensive computation or by giving an output value for each of a range of index values. The parametric model of the laser source can be relied on to generate the swept laser source characterization data. The swept laser source characterization data may be obtained from the parametric model and a real-time measurement of one or more properties of the swept laser source. A parametric model is a set of related mathematical equations in which alternative scenarios are defined by changing the assumed values of a set of fixed coefficients (i.e. parameters). The parametric model is specified by a functional relationship between model parameters, where some of the parameters can be measured in real time and other parameters are fixed or factory values. By imputing the model parameters into the parametric model, the swept laser source characterization data may be generated. The parametric model can be provided with a software program in a host PC 58 to create a digital and then analog representation, as shown in FIG. 3. The analog representation will require a D/A converter or waveform generator, as described previously. All such characterization data 26 is outputted to the arbitrary waveform generator to give a Uniform Frequency Sample Clock signal for the digitizer.

Pathway 2: Auxiliary Wavemeter Coupled with a A/D and D/A Converter

Figure 4A:
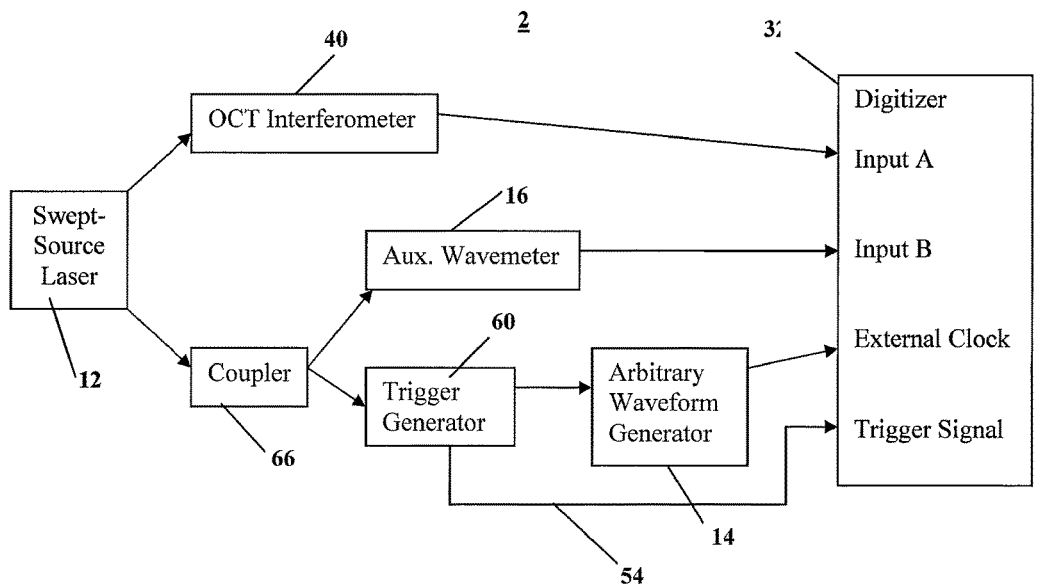
FIG. 4A is a schematic of one embodiment of Pathway 2.

In one embodiment, the Uniform Frequency Sample Clock 10 includes Pathway 2 comprising coupling the swept source 12 to the auxiliary wavemeter 16 and the A/D converter or digitizer 18, as shown in FIG. 4A. The A/D converter 18 is an electronic internal circuit that converts continuous analog signals to discrete digital numbers. The D/A converter, otherwise known as the arbitrary waveform generator 14, is then used to output a digitally-processed Uniform Frequency Sample Clock signal 30 to the external clock signal 34 input of the digitizer 32. The Uniform Frequency Sample Clock signal 30 is repeatedly outputted for each subsequent optical trigger 54 that occurs as the laser is sweeping the optical trigger is generated. The optical trigger 54 may be generated by any of the previously discussed methods.

Figure 4B:
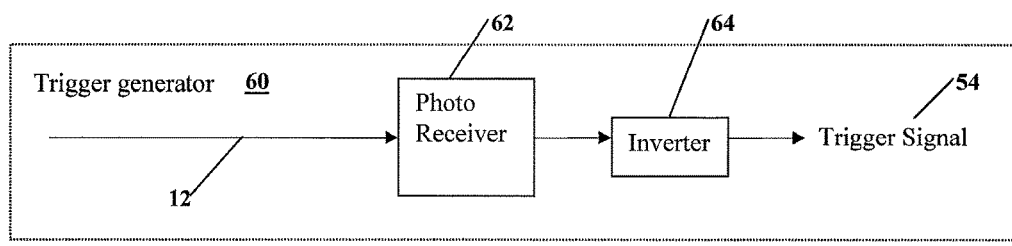
FIG. 4B is a schematic of the trigger generator.

For one embodiment of Pathway 2, a portion of the light emitted from the swept source 12 is coupled to the auxiliary wavemeter 16 and the optical trigger generator 60 via a 50/50 coupler 66 or an arbitrary splitting coupler, which splits the light into the auxiliary wavemeter 16 and the optical trigger generator 60. The auxiliary wavemeter 16 may be any type of wavemeter, including, but not limited to, a Mach-Zehnder, Michelson, or a Fabry-Perot interferometer. Fabry-Perot interferometers are preferred if the OCT interferometer 40 is phase-sensitive. If the OCT interferometer 40 system is not phase-sensitive, then Mach-Zehnder, Michelson interferometers, or etalons may be used as the auxiliary wavemeter 16. As shown in FIG. 4B, in one embodiment of Pathway 2, the optical trigger generator 60 includes a photoreceiver 62 and an inverter 64 to generate an electronic trigger signal 54, based on Transistor-Transistor Logic ("TTL"). TTL digital circuits are built from bipolar junction transistors, and resistors with both the logic gating function (e.g., AND, Inversion, etc.) and the amplifying function are performed by transistors. The optical trigger generator 60 generates the electronic trigger signal 54 according to when the swept source laser 12 light is being emitted. The trigger signal 54 is used to synchronize the digitizer 32 and arbitrary waveform generator 14 electronics when the laser has begun a sweep of its light emission. In another embodiment of Pathway 2, the optical trigger generator 60 may be derived from the tuning element in the swept laser source, either the transducer driving the tuning element or some transducer reading the tuning element (e.g., encoder or interferometric signal), which might be light based. Alternatively, the optical trigger generator 60 may be derived by sampling the light emitted from the swept laser source, where the sampling element can be one or more combinations of optical frequency selective elements, as discussed previously. Combinations of these approaches can be employed for the optical trigger generator 60.

Figure 4C:
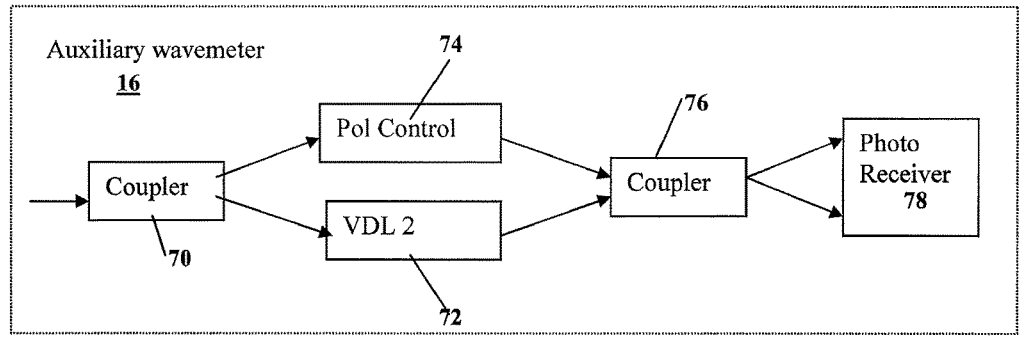
FIG. 4C is a schematic of the auxiliary wavemeter.

As shown in FIG. 4C, in one embodiment, the auxiliary wavemeter 16 is a Mach-Zehnder interferometer, where the input from the coupler 66 extends into a 50/50 coupler 70 to separate the Mach-Zehnder into two output paths. A first output path from coupler 66 extends into a Variable Delay Line VDL 72, a second output path from the coupler 66 extends to a Polarization Controller 74. The variable delay line 72 system consists of an input fiber, a retro-reflecting mirror on a translation stage, and an output fiber. A manual dial or electrical motor controls the variable length, or delay, inserted into the optical path, as selected according to various factors of the swept laser source being used. The pathlength delay determines the clock frequency. Both the polarization controller 74 and the VDL 72 extend to a 50/50 coupler 76, which recombines the separate paths of the Mach-Zehnder interferometer to dual-balanced photoreceiver 78.

Figure 5:
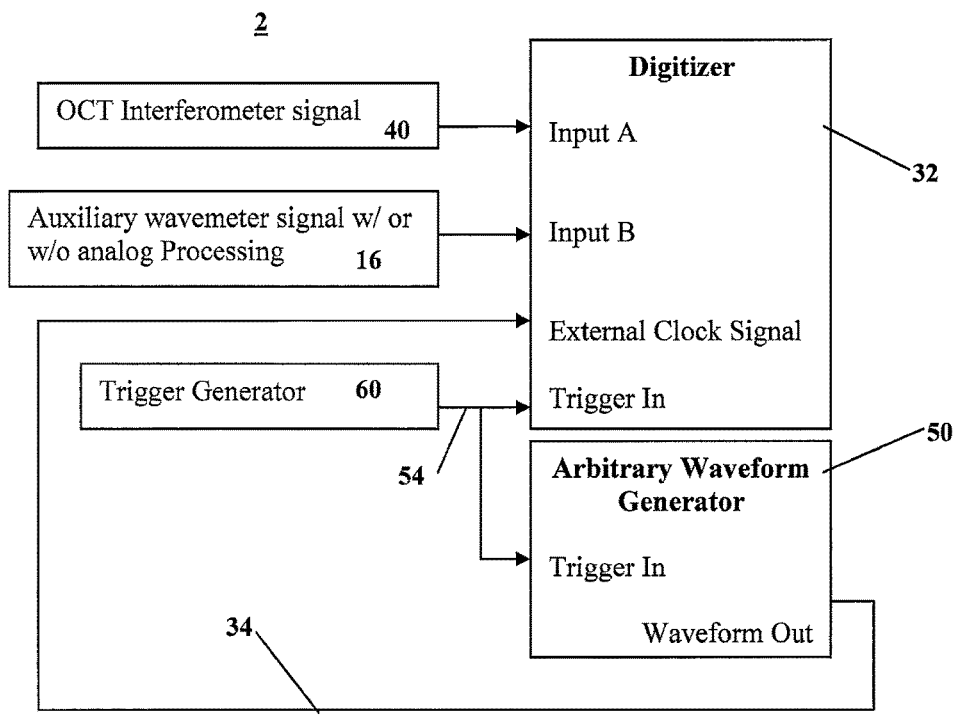
FIG. 5 is a schematic of the digitizer with the arbitrary waveform generator.

In one embodiment of Pathway 2, the Uniform Frequency Sample Clock 10 generates an external sample clock signal 34 linked to the high-speed digitizer card 32, as shown in FIG. 5. The high-speed digitizer card 32 is coupled to the output of the OCT interferometer 40, the output of the auxiliary wavemeter 16, the trigger signal 54 from the trigger generator 60, and the arbitrary waveform generator 50. The high-speed PCI digitizer card 32 can be a dual-channel high resolution 16 bit, 125 MS/s waveform for the PCI bus. The external sample clock signal 34 is derived from an auxiliary optical wavemeter photoreceiver 78 during a start-up calibration step, and then repeatedly outputted by the arbitrary waveform generator 50 for each subsequent optical trigger signal 54 that occurs as the laser is sweeping. The external clocking system of Pathway 2 allows for the wavemeter-generated clock signal to be filtered and processed in software before being outputted by the arbitrary waveform generator 14. Thus, the external clock derived from the auxiliary wavemeter 16 is regenerated by the arbitrary waveform generator 50 (Gage CompuGen) to allow acquisition of data directly in wavenumber (k) space.

Figure 6A:
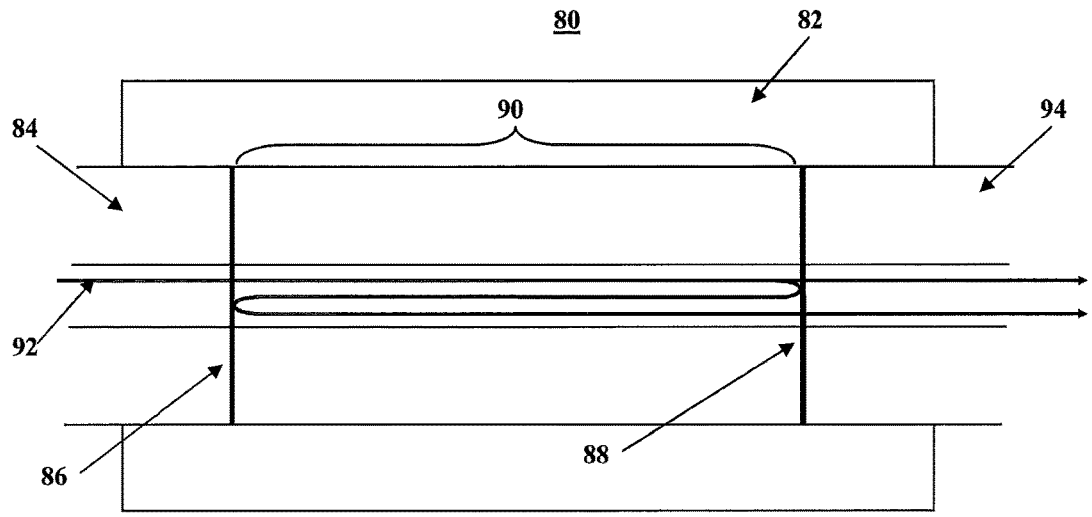
FIGS. 6A and 6B are cross-sectional view of schematics for alternative embodiments of the auxiliary wavemeter.
Figure 6B:
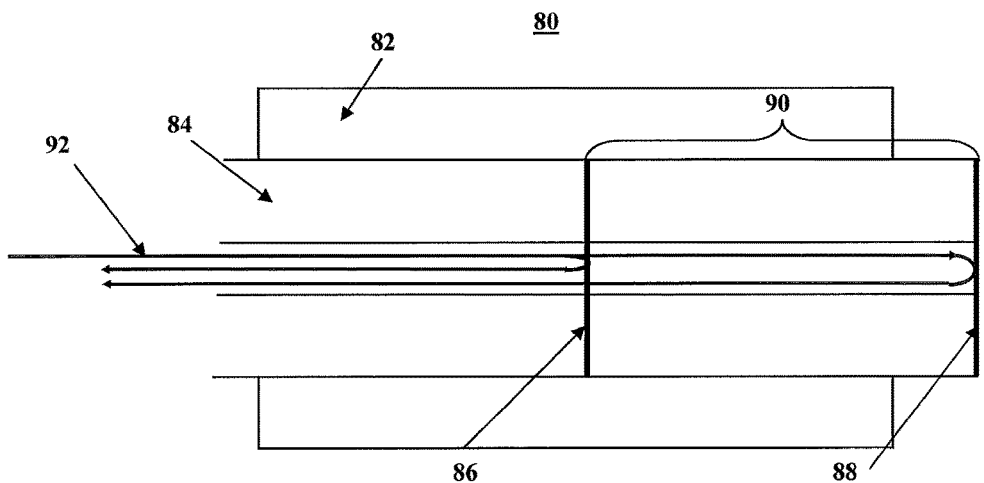

In another embodiment of Pathway 2, the auxiliary interferometer 16 is a Fabry-Perot interferometer, as shown in FIGS. 6A and 6B. FIG. 6A shows a transmission mode Fabry Perot interferometer 80 made from a ferrule 82 having an internal diameter the same OD as the optical fiber cladding connected from the coupler. The transmission mode ferrule 82 includes a single mode (SM) optical fiber 84 with a first interface 86 and a second interface 88, where each interface is coated with a metal or dielectric material to achieve a desired reflectivity. The optimum reflectivity at each interface will be chosen to maximize interference fringe visibility (i.e., matched intensity reflected from each interface into detection path) as is known in the art of fiber Fabry-Perot interferometers. Reflectivity can be controlled by coating the intermediate fiber segment 90 of the SM fiber 84 with a carefully-deposited metal or dielectric surface on each end during assembly. For example, to calculate the optimum reflectivity (R1) of the first interface in transmission mode, the following quadratic equation is solved so that the two interfering beams have the same intensity (and max visibility): $R1=(1-R1)^2$, which is solved as: R1=38.1%. Quadruple and higher-order reflections will produce harmonics, with much reduced intensity, in the fringe signal, which can processed electronically with a filter. Control of temperature of the fiber Fabry-Perot interferometer's thermal expansion/contraction to maintain a stable path-length difference provides a control for variable frequency wavemeter output.

The intermediate portion of the fiber segment 90 lies in between the first and second interface of the transmission mode ferrule. The birefringence in the intermediate fiber portion must be kept to a minimum so that both reflections will have the same polarization state. The optical path length is chosen based on desired interference fringe frequency, which can be 4 mm-6 mm for most OCT swept sources. The double-pass path length determines the clock frequency, as opposed to the single pass pathlength. The pathlength can be longer, for example in some implementations the optical path length is 10 mm, which can vary to different optical path lengths, from 5-20 mm. The pathlength delay in the Fabry-Perot determines the clock frequency as in other clocking interferometers.

The light 92 from swept laser source enters through input fiber 84 of the ferrule 82. Some light is partially reflected at the first interface 86 within the intermediate fiber segment 90 and then discarded; possibly needing an optical isolator to protect the source. The remaining light is transmitted through intermediate fiber segment 90 and partially reflected at second interface 88. The reflected portion is transmitted back to first interface, where the light is again partially reflected. Transmitted light is discarded as previously and reflected portion makes a second forward propagation through intermediate fiber segment 90 and is partially transmitted at second interface 88 into an output or collection fiber 94. This portion interferes with the portion transmitted into the output fiber from the second interface on the initial reflection. Thus the path length delay sets the sampling of the optical frequency signal. The path length delay between the two transmitted portions is twice the optical path length of the intermediate fiber segment. And the path length delay sets the sampling of the optical frequency signal. Detection of the interference fringes is accomplished after collection of the light with the output fiber, which is coupled to a photoreceiver and the high speed digitizer as the auxiliary wavemeter 16 signal, as previously indicated, to directly clock the swept source or resample the wavemeter 16 signal in a post-acquisition step.

In another embodiment of the auxiliary interferometer 16, as shown in FIG. 6B, the reflection mode Fabry Perot interferometer 80 includes the ferrule 82 having an internal diameter the same OD as the optical fiber cladding connected from the coupler. The reflection mode ferrule 82 is coupled to a polarization-insensitive circulator (not shown) and a single mode optical fiber 84 with a first interface 86 and a second interface 88, where each interface is coated with a metal or dielectric material to achieve appropriate reflectivity, as indicated previously. The SM fiber 84 includes an end portion of the fiber segment 90 that lies in between the first and second interface 86 and 88. The optical path length is chosen based on desired interference fringe frequency, which can be about 2 to about 1000 mm for most OCT swept sources. Light 92 from swept laser source enters port 1 of a polarization-insensitive optical circulator and is send outward on port 2. The fiber comprising port 2 becomes the input fiber to the inline delay device. Light 92 is partially reflected at first interface 86 within optical fiber 84. Then, the transmitted portion forward-propagates to the second interface 88, which has a maximum reflectivity. Light reflected from the second interface 88 backward-propagates to the first interface 86, where the light is partially reflected again as a second partially reflected light. The transmitted portion from the second partially reflected light beam and the reflected portion from the original incident beam then interfere and are collected on port 3 on the circulator where they are then detected by a photoreceiver, which is coupled to the high speed digitizer as the auxiliary wavemeter signal, as previously indicated.

An etalon is not substantially different from a Fabry-Perot, as the two terms are used interchangeably in the art as Fabry-Perot etalon. The Fabry-Perot etalon can be a fiber version or a free-space version. In the etalon approach, incident light (free-space) is multiply-internally reflected in a highly-controlled and wavelength-specific manner such that internal interference allows transmission of wavelengths in a periodic fashion. Frequency of this periodic transmission function depends on the thickness of the etalon and the laser sweep speed ($cm^{-1}/s$ or Hz/s). Adverse environmental effects are reduced by having light propagated along a common path, and high finesse provided by careful control of the facet reflectivity is required.

Figure 7:
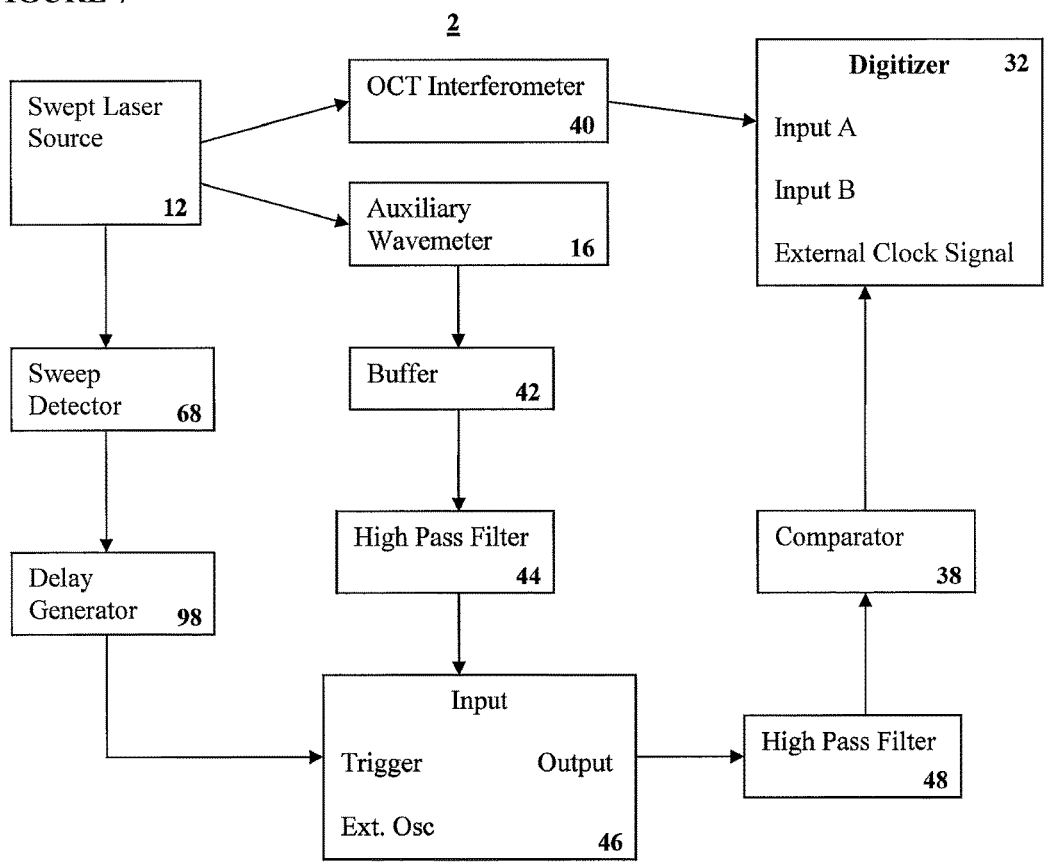
FIG. 7 is a schematic of one embodiment of Pathway 2.

In another embodiment, Pathway 2 comprises coupling the swept laser source 12 to the auxiliary wavemeter 16 and a sweep detector 68, as shown in FIG. 7. As the swept laser source 12 starts its sweep, the sweep detector 68 collects an intensity profile of the laser sweep, which is fed into a Delay Generator 98. The Delay Generator 98 has a comparator built in so that it can shape the intensity profile of the laser into a square wave. This square wave can be varied in length from 20-50 uS, depending on what is needed. This 20-50 uS wavelength is dependent on the laser can be easily modified to for different laser sweep speeds and duty cycles. This shaped square wave is then fed into a switching circuit 46.

The OCT Interferometer 40 operates normally; sending the OCT fringe signal data to the digitizer 32 that is clocked by the process that occurs with the auxiliary wavemeter 16. The auxiliary wavemeter 16 can be any of the previously described wavemeters, Mach-Zehnder, Michelson, Fabry-Perot, inline Fabry-Perot, and the like. The auxiliary wavemeter 16 creates an interference pattern that has a non-uniform frequency in time, based on the path length mismatch when the laser is operating. This auxiliary wavemeter 16 signal is converted to an electrical signal using a balanced photodetector, which is then passed into a circuit that includes a buffer 42 and a high pass filter 44. The signal is buffered for impedance matching purposes, and then the signal is directed into the high pass filter 44 to remove low frequency components than a cutoff frequency. The filtered signal is then directed into an electronic switch circuit 46. The electronic circuit switch establishes connections between links, on demand and as available, in order to establish an end-to-end circuit between devices. The connections are temporary, continuous, and exclusive in nature. When the laser power is less than the threshold level or the wavelength of the laser sweep is outside of a certain range (i.e. a false condition), the trigger signal from section is 0 volts, and 5V when the condition is true. The output of the switch circuit 46 is an external clock when a 0V signal into the trigger of the switch circuit 46. This external clock is not tied to the laser in any way and is always running. The output of the switch circuit 46 is the filtered signal from the auxiliary wavemeter 16 when the trigger voltage is 5V (when the condition is true). This satisfies the condition of some A/D cards to always have a clock on the input, even while the laser is not on.

Regardless of the output of the switch circuit 46, the signal is high pass filtered through the high pass filter 48. The signal from the high pass filter 48 is coupled into a high speed comparator 38. A comparator is a device which compares two voltages or currents and switches its output to indicate which is larger. The high speed comparator 38 converts the signal from the high pass filter into a square wave that has a voltage level compatible with the digitizer 32 external clock input parameters. The high pass filter 48 and comparator 38 help clean up the signal. The signal is then fed into the external clock on the digitizer 32 A/D card.

OCT Interferometer

Figure 8:
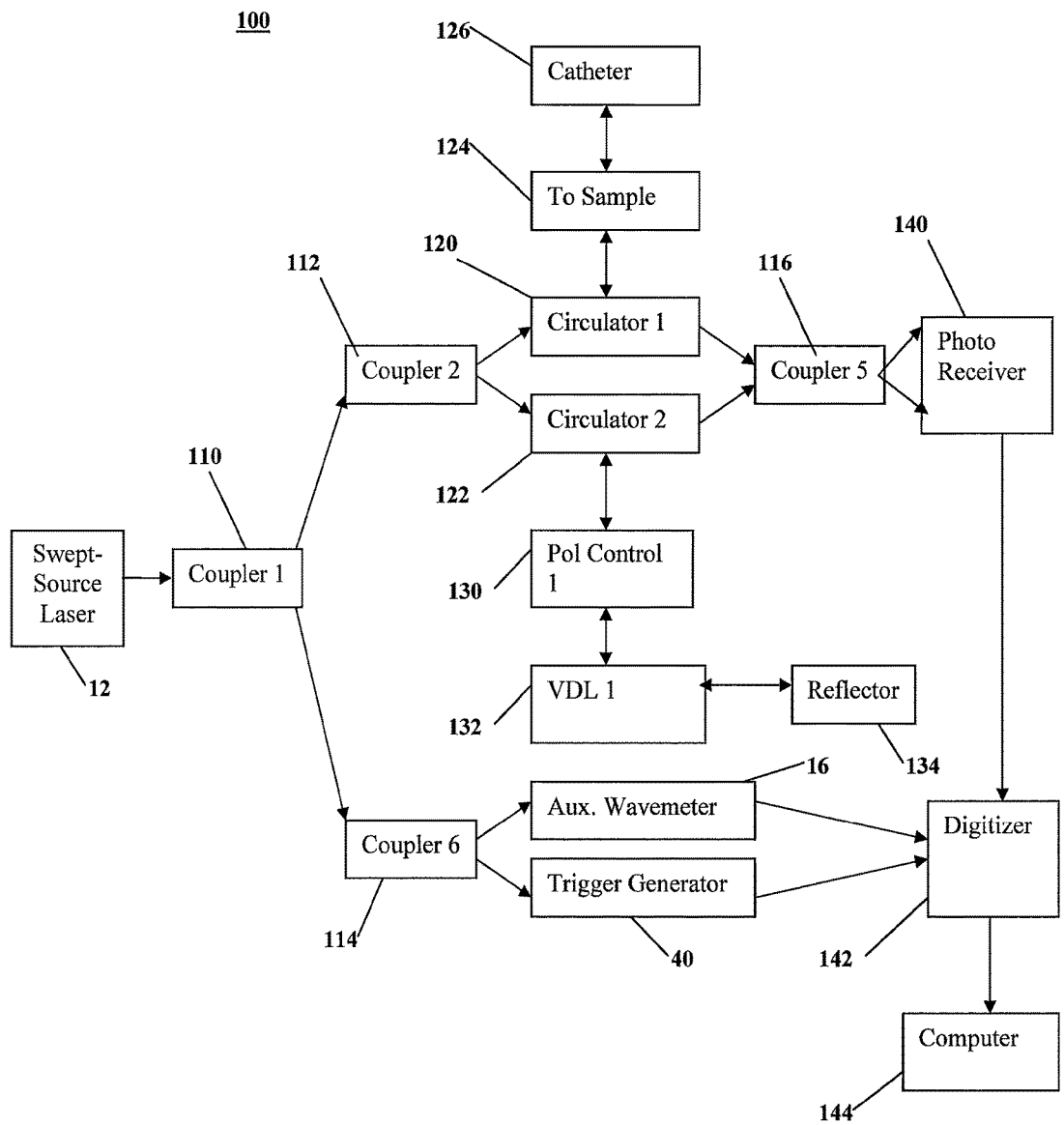
FIG. 8 is a schematic of one embodiment of the OCT interferometer.

In one embodiment, as shown in FIG. 8, the OCT interferometer 40 can comprise, a Mach-Zehnder interferometer configuration 100, which measures the complex mutual coherence function (magnitude and phase) between two non-reciprocal optical paths, one path encompassing an object under test, i.e. "the sample", and the other a reference path. Alternatively, the OCT interferometer can comprise a Michelson interferometer configuration which measures the same coherence function in a reciprocal configuration, i.e. the same splitter/coupler is used for both input splitting and output recombination. A SS-OCT system and calculations for the OCT interferometer is generally described and explained by the inventors in U.S. patent application Ser. No. 11/446,683, and Provisional Application Ser. No. 60/932,546, herein incorporated by reference.

The OCT system 100 has swept light source 12 with cascaded fiber optic couplers to subdivide the source light into three primary modules (1) the primary OCT interferometer, (2) the auxiliary wavemeter interferometer 16, and (3) the optical trigger generator 60. In one embodiment, the swept light source 12 is a High Speed Scanning Laser HSL-2000 (Santec) with an instantaneous coherence length of over 10 mm, an 110 nm Wavelength Scan Range, and a scan rate of 20 kHz. Line-arrows generally designate optical fibers coupled the elements of the OCT system 100.

As shown in FIG. 8, in one embodiment of the OCT interferometer 100, 90% of the radiant output of the swept light source 12 is split into the primary OCT interferometer by coupler 110. Coupler 110 splits light into a coupler 112 and a coupler 114. Then coupler 112 splits light 90% of the directed light to port 1 of a 3-port polarization insensitive optical circulator 120 for the sample path and 10% of the light is directed to port 1 of a 3-port polarization insensitive optical circulator 122 for the reference path. Port 2 of circulator 120 for the sample path is coupled to a sample 124. The sample path can be coupled to a probe or catheter 126 via a fiber optic rotary junction (not shown). Examples of a rotating catheter tip for the sample path include, a catheter for in-vivo imaging as described in U.S. Provisional Application No. 60/949,511, filed Jul. 12, 2007, a turbine-type catheter as described in Patent Cooperation Treaty application PCT/US04/12773 filed Apr. 23, 2004; or a rotating optical catheter tip as described in U.S. patent application Ser. No. 11/551,684; or a rotating catheter probe as described in U.S. patent application Ser. No. 11/551,684; each herein incorporated by reference for the methods, apparatuses and systems taught therein. The catheter can be located within a subject to allow light reflection off of subject tissues to obtain optical measurements, perform medical diagnosis, complete treatment, and the like.

Continuing with FIG. 8, port 2 of the optical circulator 122 is coupled to a polarization controller 130 and a Variable Delay Line ("VDL") 132 for the reference path. The VDL 132 extends to reference reflector 134. The variable delay line 132 system consists of an input fiber, a retro-reflecting mirror on a translation stage, and an output fiber. A dial controls the variable length, or delay, inserted into the optical reference path. The typical length variation is about 6 cm, while the typical time delay is about 300 picoseconds. The VDL 132 provides for larger path-length adjustments with micron-size adjustment being the smallest increments.

For the reference path, port 3 of the optical circulator 122 is then coupled to a 50/50 coupler 116, while port 3 of the optical circulator 120 is coupled to the coupler 116 for the sample path. The reference and sample paths encompass the total optical path beginning at the split in coupler 112, into ports 1 of the circulators 122 and 120, out of and back into ports 2 of the circulators 122 and 120, out of ports 3 of the circulators 122 and 120, and ending at their combination in coupler 116. The coupler 116 includes outputs 3 and 4 to a dual-balanced photoreceiver 140. The photoreceiver 140 comprise a detection element, such as an InGaAs photo-diode and a transimpedance amplifier, which converts the electrical current signal generated by photons absorbed by the photodetector element into a voltage signal that can be read by the digitizer. Typically, some gain amplification is given at this stage or in a following stage, as well as some filtering for removing noise that is outside of the relevant electrical signal bandwidth. The gained and filtered voltage signal is digitized. The OCT interferogram [S(k)] is digitized at 16-bit resolution using a high-speed PCI digitizer 142 board (AlazarTech ATS660, Toronto, Canada) coupled to the photoreceiver 140 from the primary OCT signal and the photoreceiver from auxiliary wavemeter 16. The external clock derived from the wavemeter and regenerated by the arbitrary waveform generator (Gage CompuGen) allows acquisition of OCT signal data directly in wavenumber (k) space. S(k) is converted using the Fast Fourier Transform (FFT) into the pathlength (z) domain. The magnitude of the transformed OCT A-scan [|S(z)|] represents the backscattered magnitude at depth z in the sample. The digitizer is coupled to a computer processor 144, which is a state-of-the-art workstation with a fast multi-core processor, RAID striped disk array, and large RAM space. Alternatively, the computer processor 144 includes a distributed acquisition and processing system, as described in U.S. patent application Ser. No. 11/868,334, filed Oct. 5, 2007, herein incorporated by reference.

OCT Depth Calibration and Automated Range Adjustment

Circular and cylindrical OCT scanning devices, i.e. the rotation catheter scanning devices discussed previously, sample physical space in an inherently polar coordinate system (e.g. radius and angle rather than length and width). Circular and cylindrical OCT scanning devices are applied to image physiological structures with cylindrical-like cross sections e.g., airways and blood vessel lumens). However, digital representations of the images (i.e. arrays of pixels representing numeric values) are inherently rectangular. A method for detecting and using OCT image features, either intentionally or artifactually generated, comprises automatically adjusting the depth range in polar ("radar-like") OCT images.

Polar OCT images must be converted from their rectangular representation before displaying to the viewer. Additionally, if quantitative values (e.g. lumen diameters, lumen areas, circumferences, etc.) are to be measured on the polar image, then the transformation from rectangular to polar must preserve relative distances between pixels in all dimensions (radial and angular). Generally, the OCT depth scan (y axis in rectangular coordinates) maps directly to radius and the OCT circumferential scan (x axis in rectangular coordinates) maps to some increment of 2*Pi radians (or 360°.) polar angle.

For example: y=0 (the top row of the rectangular image) maps to radius=0 (the center of the polar image) and y=$y_{sub}$max (the bottom row of the rectangular image) maps to radius=$y_{sub}$max (the perimeter of the polar image). Likewise, x=0 (the left column in the rectangular image) maps to angle=0° and x=$x_{sub}$max/2 maps to approximately 180° and x=$x_{max}$ maps to an angle of approximately 359°.

For accurate quantitative dimensional measurement in polar images, pixels mapping to radius=0 must represent the actual physical space at the center of the axis of rotation of the imaging probe, otherwise the polar image will be artificially warped (expanded or contracted) in the radial direction. However, in an arbitrary OCT image, the pixels at y=0 do not necessarily satisfy this requirement and must be shifted in the y dimension until this is satisfied before mapping to a polar representation. Differential displacements (either controlled or uncontrolled) in the path length of the sample vs. reference arms of the interferometer will shift the pixels in the y dimension.

Uncontrollable displacements can occur when using cylindrical (actually helical)-scanning fiber-optic OCT catheters; for example, when the catheter is pushed or pulled longitudinally, the fiber-optic cable can be compressed or stretched and thus a path length displacement is incurred.

The method is an automatic recognition of the uncontrolled displacement effect based on searching for image features that should be stationary (but are not due to uncontrollable displacement), and successive calibration of OCT image data so that polar representations can then be used for accurate dimensional measurements. Finally, a method is provided for subsequent removal of image features in image prior to display.

Image features used by the method are generated within the catheter itself (not within the imaged subject or surroundings) and should appear somewhat stable in depth and consistent in intensity throughout the 360°. rotation of the catheter. These include but are not limited to back reflections at interfaces between optical components (aka "ghost-lines" or "echo artifacts", these occur along the optical axis of rotating parts and thus appear as uniform circles in the polar image when no differential path length displacement occurs over the course of one catheter rotation), or reflections from the boundaries of or from within the stationary (non-rotating) catheter sheath (if it is circular in cross-sectional profile and also mechanically concentric with the rotating portion).

Steps in the automatic recognition and calibration method could include: (1) Averaging the OCT image frame along the x—(i.e. angular) dimension. This selectively enhances the feature(s) which are rotationally stable in the y dimension (i.e radius) vs. other image features generated by subject or surroundings. Efficacy of the method is improved if the image feature(s) used have high intensity relative to the surrounding pixels and if subject/environment features (noise) do not have strong circumferential symmetry; (2) Find feature(s) using peak searching, correlation, thresholding, or other pattern recognition algorithms known in the art. The efficacy of this method is improved if the range over which uncontrolled path length displacements can occur is known a priori, thus limiting the required search space; (3) Compare the y-value(s) of feature(s) found in step 2 to a pre-calibrated y-value which represents the actual physical location(s) of that feature(s) relative to the rotational axis, or to the location of a known "conjugate image" or "aliased image" of that feature(s) when using spectral-domain OCT; (4) Calibrate by shifting the OCT image pixels in the y dimension by the difference between searched feature(s) and pre-calibrated feature(s). Multiple features can be used to improve efficacy of the algorithm. After shifting the rectangular image in the y dimension, map to polar image coordinates. Radii measured to the center of the calibrated polar image will represent actual radii measured to the rotational axis in physical space. Often image features due to the catheter are unwanted for effective and distraction-free display of the subject/environment features. For example, the catheter image features could overlap the subject/environment features.

Steps to remove (or make less noticeable) the image features could include: (1) Cropping out the image feature(s) extent in the y/radial direction and in all columns/angles; (2) Calculating the average value of the pixels immediately inside and outside (above and below) of the cropped region for all columns/angles and inserting this averaged row/circumference in the cropped location. Unfortunately, the cropping operation can also remove subject/environment features and distorts the image in the radial dimension. This distortion makes measurement of accurate quantitative values on such images more complicated, because the measurement tool must then consider where pixels have and have not been cropped (or make the measurement on the un-cropped image).

Pathway 3: Auxiliary Wavemeter Coupled with an Analog Processor

Figure 9:
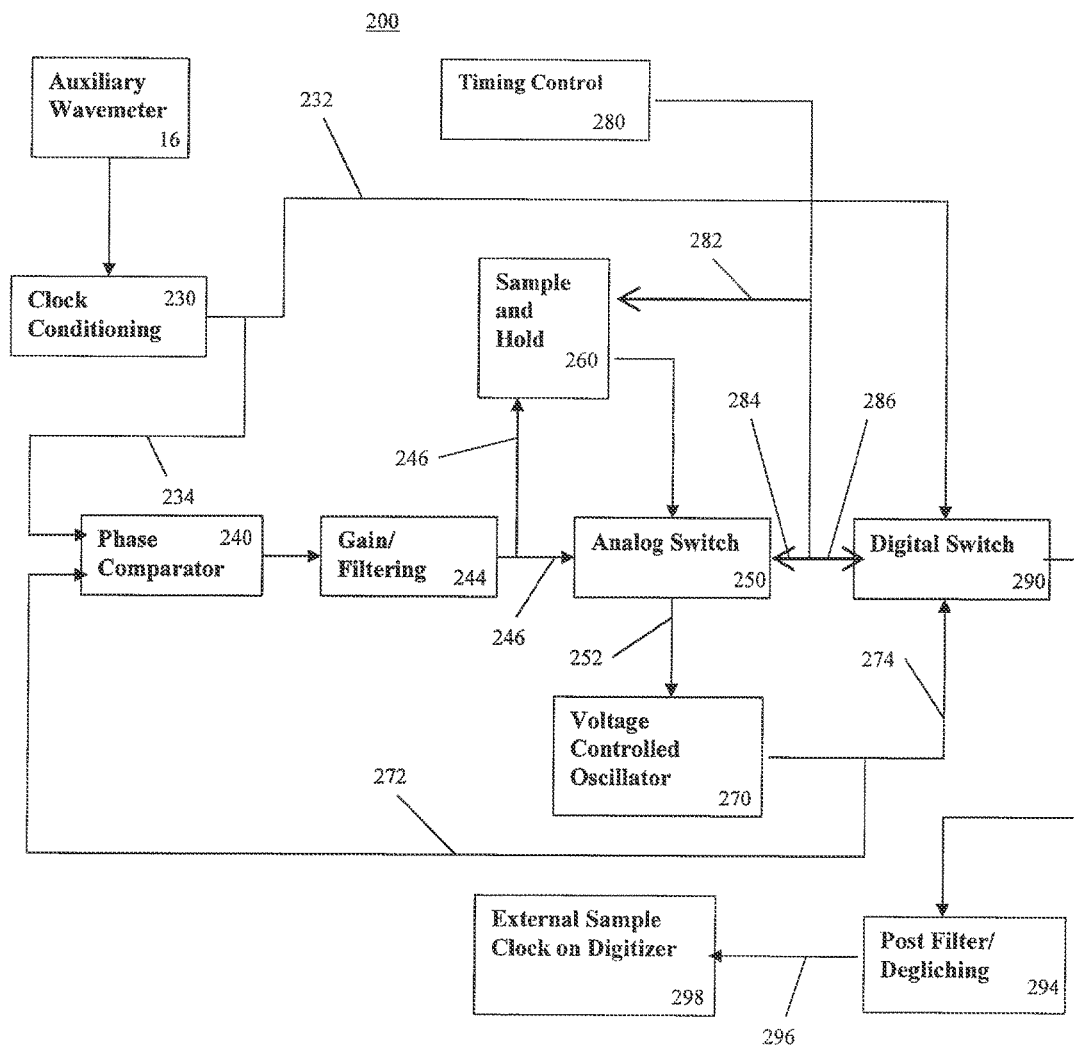
FIG. 9 is a schematic diagram of the circuit for direct external sample clocking of swept-source OCT using an optical wavemeter.

In another embodiment of the Uniform-Frequency Sample Clock 10, Pathway 3 comprises the auxiliary wavemeter 16 coupled with an analog processor, shown as in FIG. 1. The auxiliary wavemeter 16 can be any of the previously described wavemeters, Mach-Zehnder, Michelson, Fabry-Perot, inline Fabry-Perot, and the like. The analog processor can be any processor (e.g. filtering, pulse shaping, rectifying, and/or switching processor, etc.) that the wavemeter outputs to obtain a Uniform-Frequency Sample Clock signal which meets the specifications of the digitizer external clock input port. In one embodiment, the analog processor is a circuit 200 coupled to the high-speed digitizer to sample the clock signal, as shown in FIG. 9. During the laser sweep, this clock is the temporally-non-linear but the wavenumber-linear (frequency-linear) wavemeter clock. When the laser sweep is absent, this clock can be replaced with a dummy clock which has been pre-phase-locked with the k-space auxiliary wavemeter clock. Thus, high-speed digitizers are enabled to be operated in a mode where the Uniform-Frequency Sample Clock is used to directly sample the OCT signal, which avoids the need to acquire this Uniform-Frequency Sample Clock signal on a different channel and post-process data that slows down real time image display.

The sampling circuit 200 for the external sample clock signal is derived from the auxiliary wavemeter 16 during the limited duty cycle of a tunable laser source and is derived from a pre-locked (in phase and frequency) voltage controlled oscillator 270 ("VCO") during the non-sweeping segment of each duty cycle, as shown in FIG. 9. A VCO is an electronic oscillator designed to be controlled in oscillation frequency by a voltage input. The frequency of oscillation is varied by the applied DC voltage, while modulating signals may also be fed into the VCO to cause frequency modulation (FM) or phase modulation (PM); a VCO with digital pulse output may similarly have its repetition rate (FSK, PSK) or pulse width modulated (PWM). A phase locked loop (PLL) is used to sync the VCO output 274 with the optical wavemeter output before the sweep cycle is complete, at which time the external sample clock is switched from the optical wavemeter output to the output of the VCO (the dummy clock). A PLL is a control system that generates a signal that has a fixed relation to the phase of a "reference" signal. The PLL responds to both the frequency and the phase of the input signals, automatically raising or lowering the frequency of a controlled oscillator until it is matched to the reference in both frequency and phase. When the laser sweep begins again, lock is regained and the output is again switched to the k-space auxiliary wavemeter output.

The sampling circuit provides a continuous sample clock with acceptable jitter specifications to the digitizer's external sample clock input port. The locking of dummy and wavemeter clocks in phase and frequency by the PLL allows a handoff between clock sources to be free from spurious and instantaneous phase changes and frequency changes which could induce an error in the digitizer clock control circuitry.

In one embodiment, the sampling circuit 200 for direct external sampling of swept source OCT data comprises a clock conditioning block 230, a phase comparator 240, a gain-filtering block 244, a voltage controlled oscillator 270, a sample-and-hold block 260, an analog switch 250, a digital switch 290, a timing control block 280, and a post-filtering/deglitching block 294.

As shown in FIG. 9, the clock conditioning block 230 receives an input from the auxiliary wavemeter 16. The clock conditioning block 230 takes a sinusoidal analog voltage generated in the auxiliary wavemeter photodetector, and the clock conditioning block 230 filters out unwanted noise and DC component using a bandpass filter. The clock conditioning block 230 generates a digital pulse train (approximately 0-5V) at same frequency as input voltage signal and outputs 232 and 234 to the phase comparator 240 and main digital switch.

The phase comparator 240 outputs an analog voltage that is proportional to the difference in phase (and thus frequency) between the signals on its inputs, the conditioned k-space clock 230 and the VCO output 272. The phase comparator 240 can be embodied using various methods such as a charge-pump phase comparator, analog multiplier, an exclusive-NOR logic gate, i.e. an "XOR gate", etc. The phase comparator 240 outputs to the gain-filtering block 244. The gain-filtering block 244 averages the analog output voltage from the phase comparator 240 and is used to "tune" the PLL characteristics. The conditioned voltage output from the gain-filtering block 244 controls the VCO 270.

The voltage controlled oscillator 270 outputs a digital pulse train with frequency proportional to the input 252 voltage from the analog switch 250. The pulse train is negatively fed-back into an input 272 of the phase comparator 240. This closed-loop feedback or phase locked loop (PLL) causes the VCO 70 to oscillate in phase with the conditioned k-space clock 230. The phase locked loop syncs the VCO output 274 with the optical wavemeter output 16 before the sweep cycle is complete, at which time the external sample clock 298 is switched from the optical wavemeter output 16 to the output 274 of the VCO, dummy clock. When the laser begins to sweep again, lock is regained and the output is again switched to the k-space auxiliary wavemeter output 16.

The sample-and-hold circuit 260 samples and holds the output 246 voltage of the gain-filtering block 244 shortly before loss of the k-space auxiliary wavemeter clock 230. Then the sample-and-hold circuit 260 uses the analog switch 250 applied to the input 252 of the VCO 270. This maintains the VCO 270 output 272, 274 with the same phase and frequency as it was operating before loss of the k-space auxiliary wavemeter. Sample and hold operation is controlled from a signal 282 in the timing control block 280.

The analog switch 250 changes the input 52 to the VCO 270 between two analog sources (1) the sample-and-hold block 260, during dummy clock operation, and (2) the gain-filtering block 244 during wavemeter operation. The analog switch 250 is controlled from a signal 284 in the timing control block. The digital switch 290 changes the output of the entire clocking circuit between the digital conditioned auxiliary wavemeter clock 230 output 232 and the VCO 270 output 274 clock (when sweep is not present). The digital switch is controlled from a signal output 286 from the timing control block 280.

The timing control block 280 orchestrates analog switching 284, digital switching 286, and sample-and-hold operation 282 based on a trigger input signal from the swept laser source or other threshold detector. The post-filtering/deglitching block 294 removes any spurious glitches caused by switching, insures a strong full-range digital signal 296 is available for the digitizer external sample clock input.

Pathway 4: Auxiliary Wavemeter Coupled with an Analog Processor and D/A Converter In another embodiment of the Uniform-Frequency Sample Clock 10, Pathway 4 comprises the auxiliary wavemeter 16 coupled with the analog processor 20, the A/D digitizer 18, and a D/A converter 14, as shown in FIG. 1. Alternatively, a software processing step may be included after the D/A converter, or between the A/D digitizer and the D/A converter. The auxiliary wavemeter 16 can be any of the previously described wavemeters, Mach-Zehnder, Michelson, Fabry-Perot, inline Fabry-Perot, and the like. The analog processor 20 can be any processor (e.g. filtering, pulse shaping, rectifying, and/or switching processor, etc.) that the wavemeter 16 outputs to obtain a Uniform-Frequency Sample Clock signal, which meets the specifications of the digitizer external clock input port. In one embodiment, the analog processor 20 is the circuit 200 coupled to the high-speed digitizer to sample the clock signal, as shown in FIG. 9. During the laser sweep, this clock is the temporally-non-linear but wavenumber-linear (frequency-linear) wavemeter clock. When the laser sweep is absent, this clock can be replaced with a dummy clock which has been pre-phase-locked with the k-space auxiliary wavemeter clock. Thus, high-speed digitizers are enabled to be operated in a mode where the Uniform-Frequency Sample Clock is used to directly sample the OCT data signal, which avoids the need to acquire this Uniform-Frequency Sample Clock signal on a different channel and post-process data that slows down real time image display.

The analog processor 20 outputs to an A/D converter 18, which then outputs to the D/A converter. Alternatively, the software processing is included after the D/A converter, where the digitized signal is processed to a software clock signal that is input to the D/A converter, and then output to the External Clock input on the D/A converter. The D/A converter 14, is the arbitrary waveform generator, outputs the generated Uniform-Frequency Sample Clock signal for each laser sweep, triggered by an electrical synchronization pulse derived from the swept-source laser output. The external clock signal is derived from the analog processor 20 during the start-up calibration step, and then repeatedly outputted by the arbitrary waveform generator 14 for each subsequent optical trigger signal that occurs as the laser is sweeping. The Uniform Frequency Sample Clock signal is sent to the digitizer to allow the acquisition of data directly in wavenumber (k) space. From the auxiliary wavemeter, D/A converter, and then the A/D converter, and repeatedly generating the clock signal, the option of inserting a software processing step between the A/D and D/A steps remains.

Pathway 5: Auxiliary Wavemeter Coupled to the Swept-Source

In another embodiment of the Uniform Frequency Sample Clock 10, Pathway 5 includes coupling the swept source to the auxiliary wavemeter 16 and to the digitizer 32, without any pre-processing, as shown in FIG. 1. The auxiliary wavemeter 16 can be any of the previously described wavemeters, such as the Mach-Zehnder, Michelson, Fabry-Perot, inline Fabry-Perot, and the like. Alternatively, the auxiliary wavemeter 16 may be a Mach-Zenhder or Michelson interferometer depending on the OCT system employed. The auxiliary wavemeter 16 outputs a periodic signal uniformly spaced in wavenumber. The auxiliary wavemeter 16 output is used as an external clock for the High-Speed digitizer so that the OCT signal date is digitized uniformly in the wavenumber domain [S(k)]. Digitizing the OCT signal data uniformly in the wavenumber domain allows direct Fourier-transformation into the pathlength (z) domain and construction of the OCT image without time-intensive remapping. Following this approach, the nonlinear sweep characteristic of the tunable laser source is effectively removed and OCT images can be displayed in real-time.

Pathway 6: Auxiliary Wavemeter and Gas Cell Calibration Coupled to Swept Source

Figure 10A:
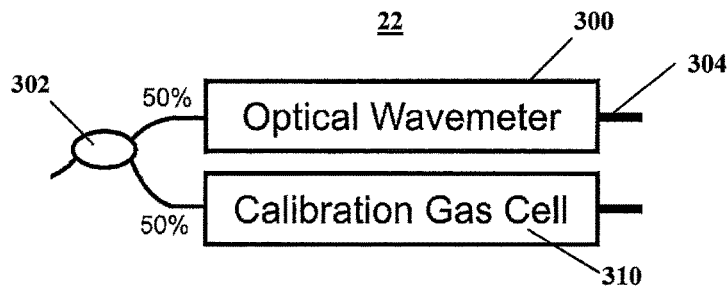
FIG. 10A is a schematic of a Calibration Gas Cell and the auxiliary wavemeter coupled from the swept source laser.

In another embodiment of the Uniform Frequency Sample Clock, Pathway 6 includes coupling the swept source 12 to the uniform frequency sample clock generator 22, as shown in FIG. 1. The uniform frequency sample clock generator 22 includes an optical wavemeter 300 and a gas cell calibration 310, as shown in FIG. 10A. A 50/50 coupler 302 splits the light from the swept source 12 to the optical wavemeter 300 and the gas cell calibration 310. The optical wavemeter 300 can be any of the previously described wavemeters, such as the Mach-Zehnder, Michelson, Fabry-Perot, inline Fabry-Perot, and the like. Alternatively, the optical wavemeter 300 may be a Mach-Zenhder or Michelson interferometer depending on the OCT system employed. The optical wavemeter 300 outputs a periodic signal uniformly spaced in wavenumber. The optical wavemeter output 304 is used as an external clock for the High-Speed digitizer so that the OCT signal data is digitized uniformly in the wavenumber domain [S(k)]. Digitizing the OCT signal data uniformly in the wavenumber domain allows direct Fourier-transformation into the pathlength (z) domain and construction of the OCT image without time-intensive remapping. Following this approach, the nonlinear sweep characteristic of the tunable laser source is effectively removed and OCT images can be displayed in real-time.

Figure 10B:
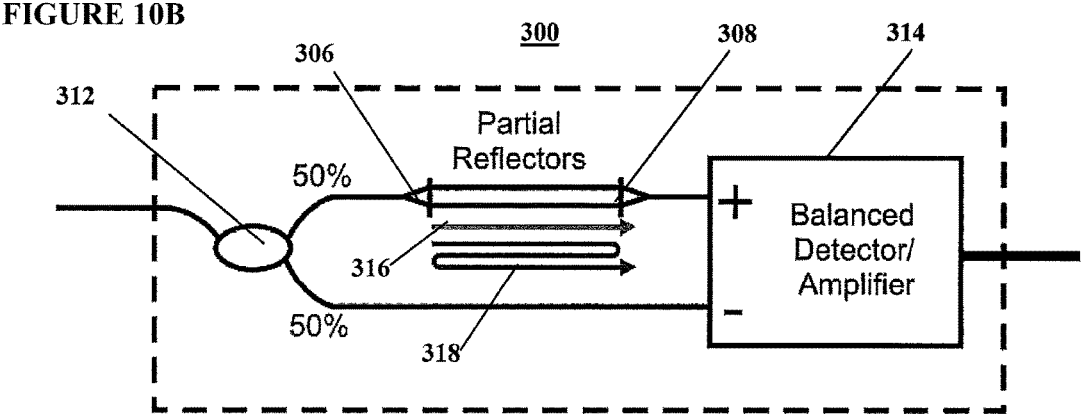
FIG. 10B is a schematic of the optical wavemeter where light making a single-pass 316 and a triple-pass 318 between partial reflectors interferes and produces a periodic signal uniformly spaced in wavenumber (k)

In one embodiment, the optical wavemeter 300 is a fiber-based Fabry-Perot interferometer with a pathlength difference generated by two in-line partially reflecting surfaces 306 and 308, as shown in FIG. 10B. A single-pass of light 316 and a triple-pass of light 318 between the partial reflectors 306 and 308 interferes and produces a periodic signal uniformly spaced in wavenumber (k). The pathlength difference is selected to produce a fringe output in wavenumber (k) space corresponding to Nyquist sampling of the longest detectable pathlength difference. The longest detectable pathlength can be a function of various factors and is always limited by the coherence length of the laser source. In cardiovascular applications, a fairly long detectable pathlength on the order of 10 min may be applied. With swept laser sources, the pathlength can be as long as a few meters (2000 mm); however, the sweep may be very slow (10 sweeps/s). Sources with a longer coherence length (detectable pathlengths) that have a faster sweep speed, with a range of 2-2000 mm. Sources with very long coherence lengths can use multiplexing principles, as described in patent application entitled "OCT Using Spectrally Resolved Bandwidth, U.S. patent application Ser. No. 11/446,683. The Uniform Frequency Sample Clocking pathways are applicable to multiplexed OCT as well.

The partial reflecting surfaces 306 and 308 are encased in a mechanically and thermally isolated enclosure to insure phase stability. A 50/50 splitter 312 and parallel balanced detector 314 is incorporated in the optical wavemeter 300 to reduce noise and improve dynamic range, as shown in FIG. 10B. Harmonics generated by higher order passes between the surfaces are effectively suppressed by the cumulative reflectivity losses and roll-off due to the finite instantaneous coherence length of the laser source (10 mm). The output of the wavemeter 300 is electrically pre-filtered and amplified into a robust external clock for the high speed digitizer/analog-to-digital ("A/D") converter.

Figure 10C:
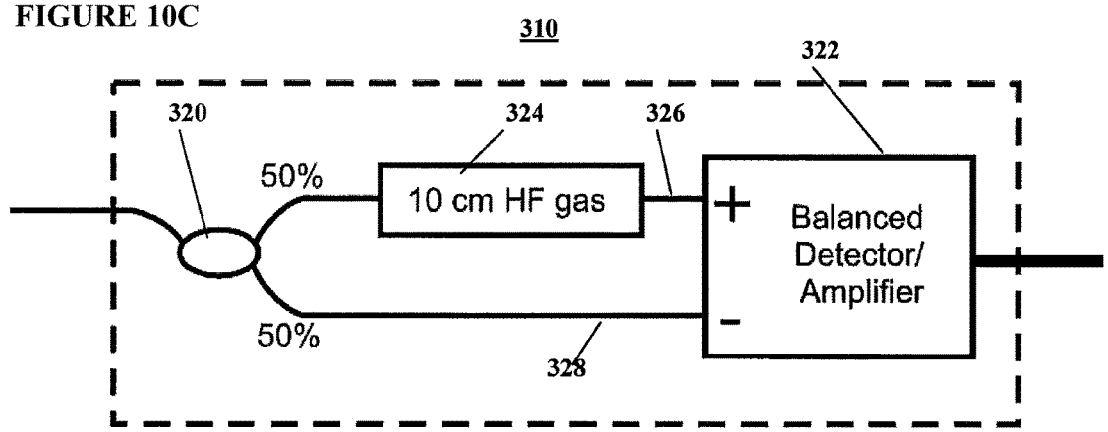
FIG. 10C is a schematic of the calibration gas cell.

As shown in FIG. 10C, the calibration gas cell 310 receives 50% of the light source from the coupler 302, where 50% of the light is split by a 50/50 coupler 320 to a balanced photodetector/amplifier 322. In one embodiment, the calibration gas cell 310 includes a hydrogen fluoride ("HF") gas cell 324 (Wavelength References, Mulino, Oreg.) with a 10 mm pathlength and a calibrated absorption fingerprint in the 1250-1350 nm spectral range for the balanced detection scheme. Alternatively, other gas cells can be used as the calibration gas cell 310, with well-known wavelength absorption bands and the pathlength selected according to the swept laser source. The well-known absorption fingerprint bands in the HF gas cell 324 result in a reduced detected intensity in the light transmitted through the gas cell 324, and as such provide a metric on the absolute lasing wavelength at those digitized sampling times. The sample number or sampling time scale can thus be converted to absolute wavelength at one or more samples, depending on the number of absorption lines. The detected wavemeter photocurrent signal 328 and the detected gas cell photocurrent signal 326 are combined in the digitizer to provide the relationship between the sample number or sampling time and lasing wavelength throughout the entire sweep. The detected photocurrent signal 326 from the gas cell is digitized concurrently with the OCT signal data and correlated with the known HF fingerprint to determine the wavenumber bias ($k_o$) of the swept source laser. Knowledge of wavenumber bias ($k_o$) allows accurate determination of the absolute wavenumber of each digitized sample throughout the spectral sweep, effectively removing any wavenumber offsets and/or phase instabilities in the laser source, wavemeter and sampling electronics.

The uniform-frequency sample clock signal which is based on the auxiliary wavemeter represents uniform intervals in wavenumber (k) biased by an unknown absolute wavenumber ($k_o$). Unfortunately, since the wavenumber bias ($k_o$) can vary between successive laser sweeps as a result of inherent instabilities in the tunable laser output spectrum, $k_o$ must be measured for each laser sweep for highly sensitive phase measurements. Gases with molecular absorption lines at NIST-calibrated wavenumbers provide unmatched stability and are used to calibrate optical spectra in a variety of high-precision spectroscopy applications.

Gas Cell Trigger

Figure 11:
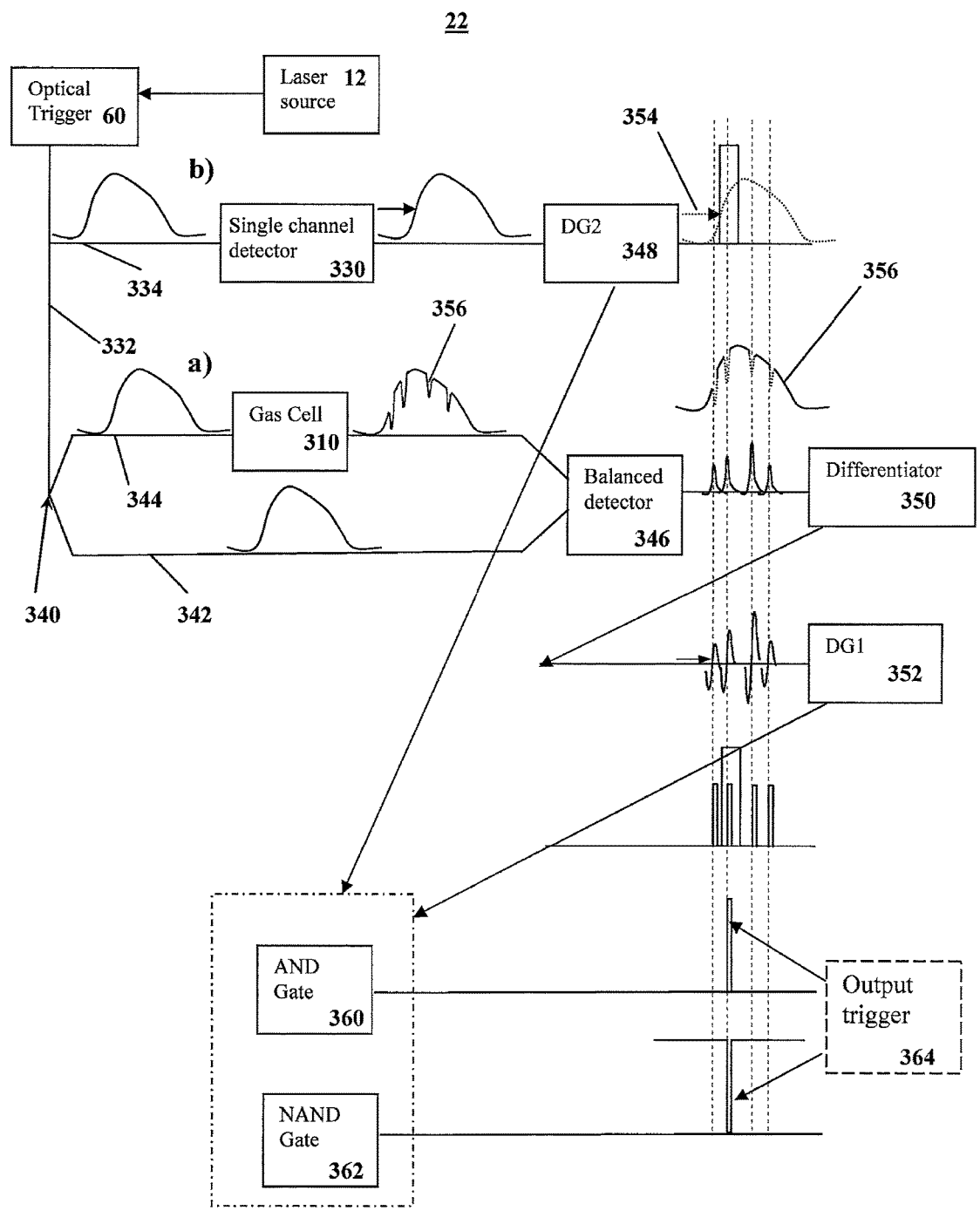
FIG. 11 is a schematic of one embodiment of Pathway 6.

As shown in FIG. 11, in another embodiment of the uniform frequency sample clock generator 22 includes coupling the laser swept source 12 to a single channel detector 330 and the gas cell 310. The laser swept source 12 power from the optical trigger 60 channel is divided into the gas cell channel 332 and a window channel 334 with the use of a coupler (not shown). The photocurrent of light passing through the gas cell 310 provides a more repeatable and stable optical trigger. An intensity-threshold optical signal can suffer from variations in intensity of the laser while an absorption line in a gas cell does not vary and can provide a highly stable wavelength reference. The gas cell channel 332 and the window channel 334 propagate light simultaneously. The gas cell channel 332 may include >90% of the total trigger channel optical power. A coupler 340 is used to split the light into a reference channel 342 and a gas channel 344. In the gas channel 344, light passes through the gas cell 310 and a gas cell pulse 356 is outputted to one of the inputs of the balanced detector 346, while the reference light is directly outputted to the second input of the detector 346. The output voltage of the detector 346, which consists of pulses corresponding to the gas cell 310 absorption lines, is used as the input of a differentiator 350. The differentiator 350 is an electronic device where the output is the derivative of the input. For example, the differentiator may be a high pass filter. By differentiating the balanced detector 346 output, the maximums of the absorption lines are replaced with a zero crossing voltage. To produce the Transistor-Transistor Logic (TTL) pulses with rising edges corresponding to the central wavelength of the absorption gas cell 310 lines, a delay generator 352 (DG1) is coupled to the output of the differentiator 350. The level of voltage that used for generating the pulses should be several fold (by absolute value) above the RMS noise level to exceed the noise floor level and avoid generating pulses from noise. The time duration of the pulses should be at least several times less than distance between neighbor gas cell pulses. The time duration of the window pulse should be at least several times less than time between neighboring gas cell absorption line pulses to prevent false triggering (during one A-scan window pulse should be always overlapped with the only selected gas cell pulse).

The window channel 334 may include about 10% of the total power of the trigger channel. The light in the window channel 334 is detected with the single channel detector 330, so the shape of the detected voltage is repeating the shape of the laser sweep. The output of the single channel detector 330 is coupled to a delay generator 348 (DG2), which is used to produce a window pulse 354. The window pulse 354 is used to select one of the gas cell pulses 356 among others. The position during the sweep where the window pulse 354 starts is adjusted with the voltage level. The start position and width of the window pulse 354 are chosen so the window pulse 354 should totally cover one of the gas cell pulses 356. Since the gas cell pulse 356 is fixed in the wavenumber domain the window pulse 354 is uttering in the wavenumber domain from sweep to sweep. Therefore, width of the window pulse 354 should be several times wider than the selected gas cell pulse 356 width, so that the window pulse 354 covers the gas cell pulse 356 for every sweep. The window pulse 354 does not cover any of the neighboring gas cell pulses 356.

The outputs from DG1 352 and DG2 348 are used as input of a logical element AND gate 360 or NAND gate 362. The main condition for the logical element is its output when both inputs are high (logical 1) should be different from any other possible input logical states. The output of the logical element is the single TTL pulse with regulated width which is fixed at a specific wavelength and can be directly used as a gas cell trigger 364 for acquisition of the OCT signal data.

The gas cell trigger 364 is tightly connected with a reference wavelength, where the source of the reference wavelength is the gas cell 310. The gas cell 310 is a hermetic capsule containing a known gas, as describe previously. The central wavelength of absorption lines of the gas depend on molecular energy levels and practically do not depend on the external conditions such as temperature. If the swept laser source is centered at 1310 nm, then the gas cell 310 should have appropriate corresponding centered absorption lines. The need for the trigger 364 fixed at selected wavelength is a particular interest for phase sensitive OCT, where phase is determined as $$\varphi = kn\Delta z = \frac{2\pi n \Delta z}{\lambda},$$

where n is the refractive index, $\Delta z$ is the in pathlength difference between the sample and reference arms of OCT interferometer, $\lambda$ is the wavelength of light. Therefore, to have $\Delta\Phi=0.1$ at $\Delta z=0.2$ mm, the uncertainty of wavelength should be <10 pm. The sweep to sweep wavelength dependence of the swept source is several orders greater. Using the Pathway 6, the uncertainty is <2 pm for a 20 kHz scan rate of the swept source (with increasing swept source scan repetition rate the uncertainty of the trigger position increases linearly). Phase sensitive OCT provides additional contrast that may be color coded onto OCT intensity images.

Figure 12:
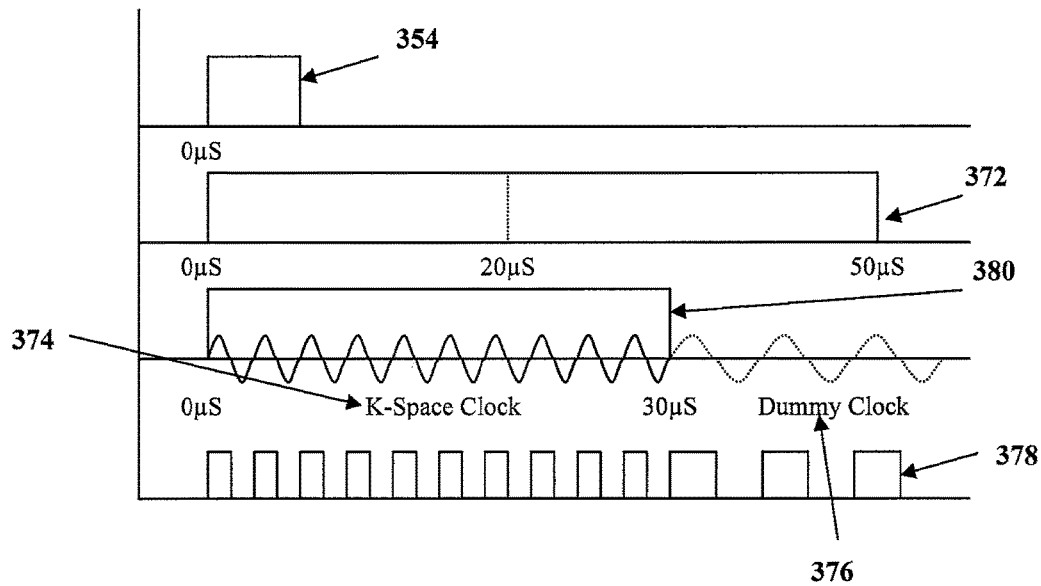
FIG. 12 is a graph schematic of one embodiment of external clock circuitry.

The gas cell trigger may be used for any OCT imaging system. The need for a trigger depends on the stability (instability) of the laser source. If the source is highly spectrally stable in time (i.e. the drive signal of the tuning element) then need for a gas cell trigger is less. Generally, the gas cell can provide a highly stable trigger. After the gas cell trigger 354 has been produced, the trigger 354 may be split into two signals. One signal is used to trigger the A/D digitizer card (Alazar) to start acquiring A-scans, and the other signal is directed to trigger the external clock circuitry 370, as shown in FIG. 12 The external clock circuitry 370 comprises a delay generator and a k-space/dummy clock switching circuit D. The delay generator comes first and uses an edge detect to sense when the differentiation circuit (trigger from the gas cell circuitry, 354) has gone high. After the edge has been detected, the delay generator outputs a 5V signal 372, where the time duration may be fixed using a resistor-capacitor combination. Time duration of the 5V pulse from the delay generator is selected to ensure sufficiently high signal to noise ratio of the K-space clock. In one embodiment, the delay generator can be programmed to provide a pulse duration from (20-50) μs. The 5V signal pulse 372 goes into the clock circuitry 370.

The clock circuitry 370 is composed of a buffer amplifier, a high pass filter, a switching network that can switch between a k-space 374 and a dummy clock 376, another high pass filter, and a comparator that converts the sine wave of the k-space 374 to a TTL signal 378. The resulting clock has a constant step in wavenumber space (k) during the (20-50) is of the pulse duration from the delay generator 380 and constant duration in other time periods. The OCT data signal is acquired uniformly in wavenumber space 374 provided by the external clock circuitry 370.

As shown in FIG. 12, the original pulse from the gas cell circuitry 354 is used to produce the (20-50) μs pulse from delay generator 380 to be used to generate switching between k-space 374 and dummy clocks 378. The TTL pulse train 378 is produced from a sinusoidal signal and used as a final clock at the external clock input of the digitizer (ADC board).

Common Path OCT Interferometer

Figure 13:
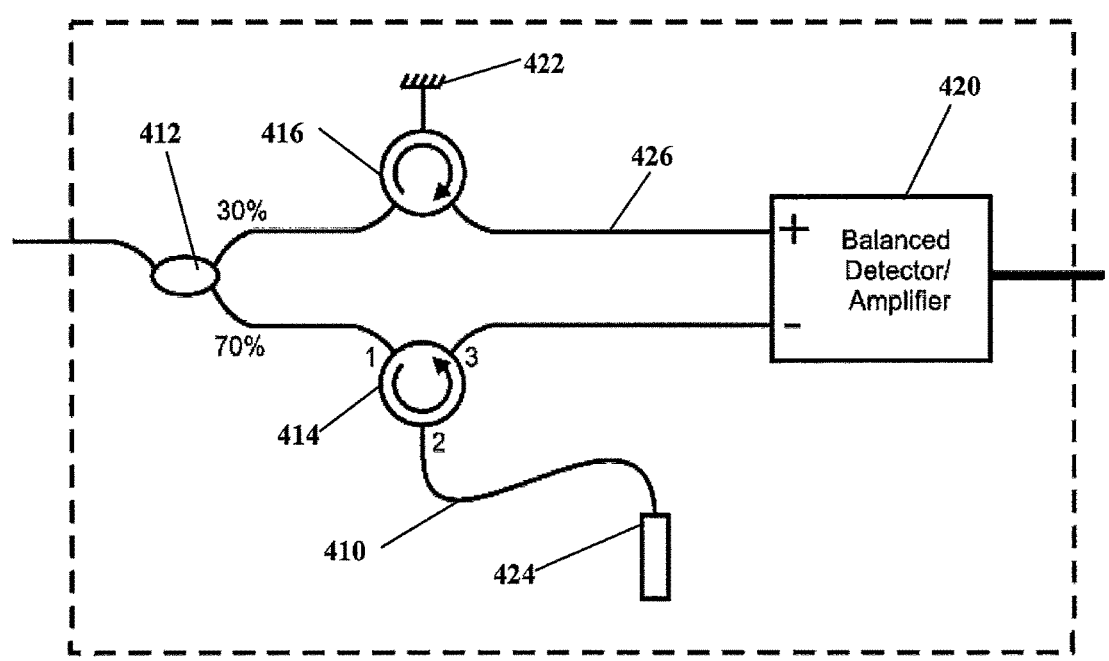
FIG. 13 is a schematic of common-path OCT interferometer in phase-sensitive Fourier Domain OCT.

In one embodiment, the OCT interferometer 40 is a common path interferometer 400, as shown in FIG. 13. The common path interferometer 400 comprises a Phase-Sensitive Fourier Domain OCT system 400 ("PS-FD-OCT") system wherein reference and sample light propagate in a common optical path 410. The common optical path 410 can propagate in an optical fiber, free space or some other material. Any environmentally induced perturbations in the common path experience common-mode rejection and phase-stable OCT signal data results. Some portion of the common optical path needs to be different, that is some portion of the sample path is distinct from the reference path. So while the reference and sample share some portion of the path, some portion of the sample path is distinct from the reference path.

As shown in FIG. 13, the optical layout of the common-path OCT interferometer employs a coupler 412 splitting light to a 3-port polarization-insensitive optical circulator 414 and a 3-port polarization-insensitive optical circulator 416. The circulator 414 includes a source light input on port 1, common reference and sample paths on port 2, and the output to a balanced photoreceiver 420 on port 3. Light is split (30%) to the circulator 416 from the input channel to a variable reflector 422 to reduce noise and improve detector dynamic range for the balancing channel 426 of the photoreceiver 420. The variable reflector 422 in the balancing channel insures equal power levels and spectral shape on the balanced detector's 420 two photodiodes. The distal end of the common-path fiber is terminated with a focusing gradient-index 424 (GRIN) lens. The GRIN lens 424 is optimized for <−65 dB return loss to minimize interference from spurious back-reflections, and may include a working distance of 5 mm and focused spot size of 20 um. A wedged 50% beam-splitter is aligned in the beam to provide a reference reflection. The sample may be positioned on two motorized linear translation stages and actuated in a raster pattern to create three-dimensional OCT volume scans. Alternatively, the sample path can be coupled to a scanning system with a flat and calibrated optical field. Such scanning systems are known in the art of optical design and can include for example a galvanometer, a scanning lens and field flattener lens. Alternatively, the sample path can be coupled to a probe or catheter via a fiber optic rotary junction. Examples of a catheter for in vivo imaging in the sample path include, U.S. Provisional Application No. 60/949,511, filed Jul. 12, 2007, a turbine-type catheter as described in Patent Cooperation Treaty application PCT/US04/12773 filed Apr. 23, 2004; or a rotating optical catheter tip as described in U.S. patent application Ser. No. 11/551,684; or a rotating catheter probe as described in U.S. patent application Ser. No. 11/551,684; each herein incorporated by reference for the methods, apparatuses and systems taught therein. The catheter can be located within a subject to allow light reflection off of subject tissues or nanoparticles to obtain optical measurements, medical diagnosis, treatment, and the like.

Figure 14:
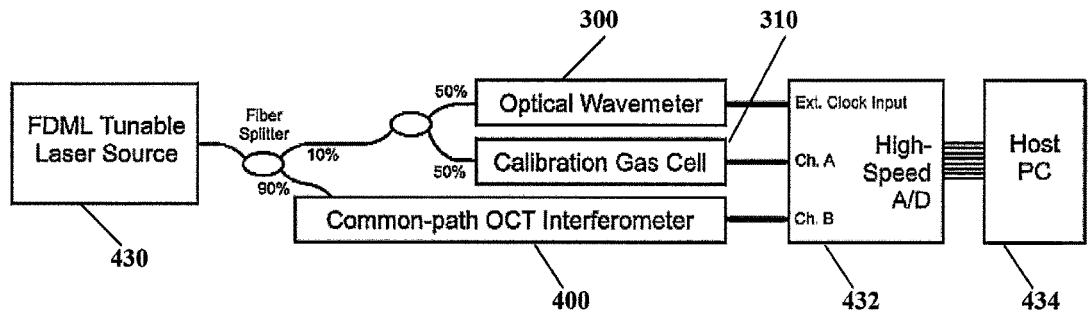
FIG. 14 is a block diagram of phase sensitive Fourier-domain OCT instrument with the Real-Time Imaging Clocking system.

As shown in FIG. 14, the common path OCT interferometer 400 is coupled to a FMDL tunable laser source 430, where the FMDL source 430 is coupled to the optical wavemeter 300 and the calibration gas cell 310. The OCT interferogram [S(k)] and calibration gas cell signature are digitized at 16-bit resolution on two channels of a high-speed PCI digitizer 432 board (AlazarTech ATS660, Toronto, Canada). The external clock derived from the wavemeter 300 output and allows acquisition of data directly in wavenumber (k) space. $S(k_o)$ is shifted to remove any bias as determined by the gas cell 310 absorption fingerprint and converted using the Fast Fourier Transform (FFT) into the pathlength (z) domain. The transformed OCT A-scan [S(z)] is a complex signal $\{|S(z)|, \arg[S(z)]\}$ representing the backscattered magnitude and phase at depth z in the sample. The digitizer 432 is coupled to a host PC 434 is a state-of-the-art workstation with a fast multi-core processor, RAID striped disk array, and large RAM space. The complex signal representing the A-scan may be used as input into an algorithm to solve the inverse problem to estimate the refractive index profile (n(z)) of the sample.

FIG. 15 compares axial point spread functions and OCT images generated with both uniform time sampling and the uniform frequency sample clocking approach 10 using the previously discussed Pathways. The graph shows the OCT point spread functions vs. depth for an internally clocked/remapped scheme 440 and the novel externally clocked scheme 442; the larger height and narrower width of the externally clocked functions results in greater signal-to-noise ratio ("SNR'), improved axial resolution, and suppressed artifacts, especially at larger depths (2.5 mm-3.5 mm). Additionally, the externally clocked scheme is less computationally and bandwidth intensive.

Multiple Uniform Frequency Clock Signals

Figure 18:
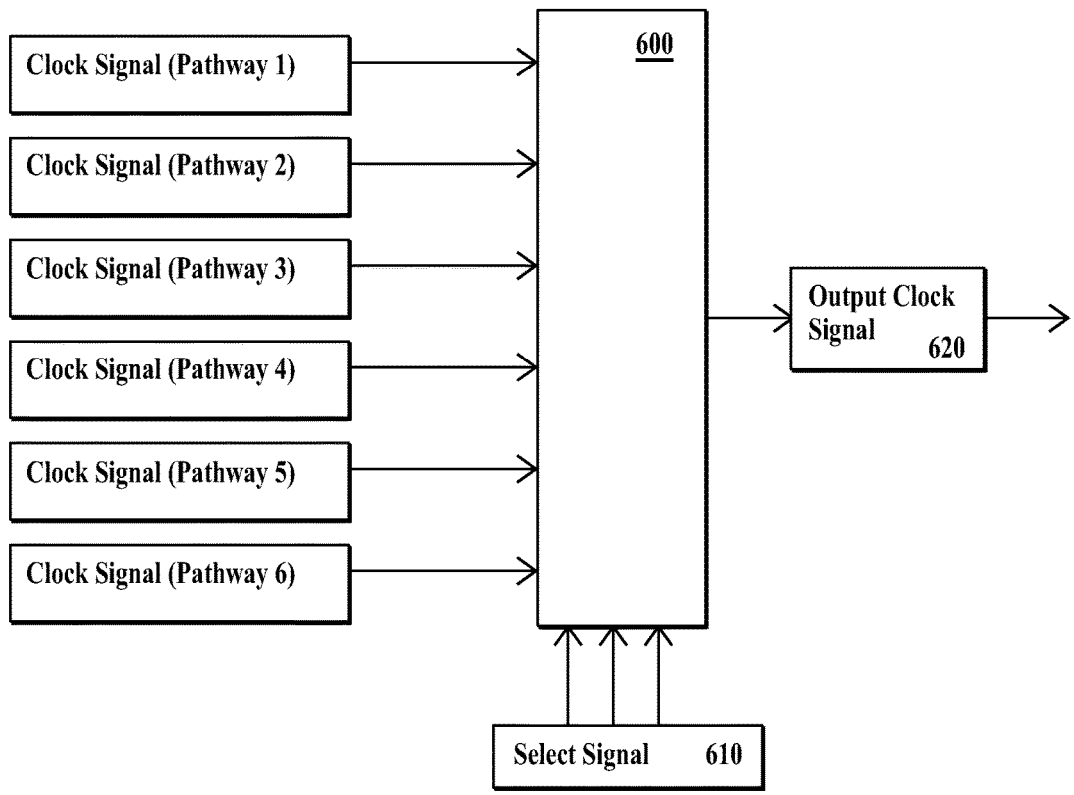
FIG. 18 is a schematic of the demultiplexer coupling multiple clock signals from various pathways.

For each acquisition channel, one clock signal may be active at a given time, which may be switched between different clock signals in any particular combination or order. Alternatively, more than one uniform frequency clock signal may be synchronously coupled to the ADC channel through a circuit that combines/alters the two clock signal to produce a synchronous signal that reveals something more than just one clock signal. As shown in FIG. 18, multiple clock signals from various pathways is inputted into a demultiplexer 600, where the demultiplexer has an input (possibly digital) that selects one of the input signals. The demulitiplexer would be applicable for the real time clock signal derived from the wavemeter and a backup clock signal is provided just in case the real-time circuitry fails or is intermittent in one way or another.

Phase Sensitive OCT System

Figure 16:
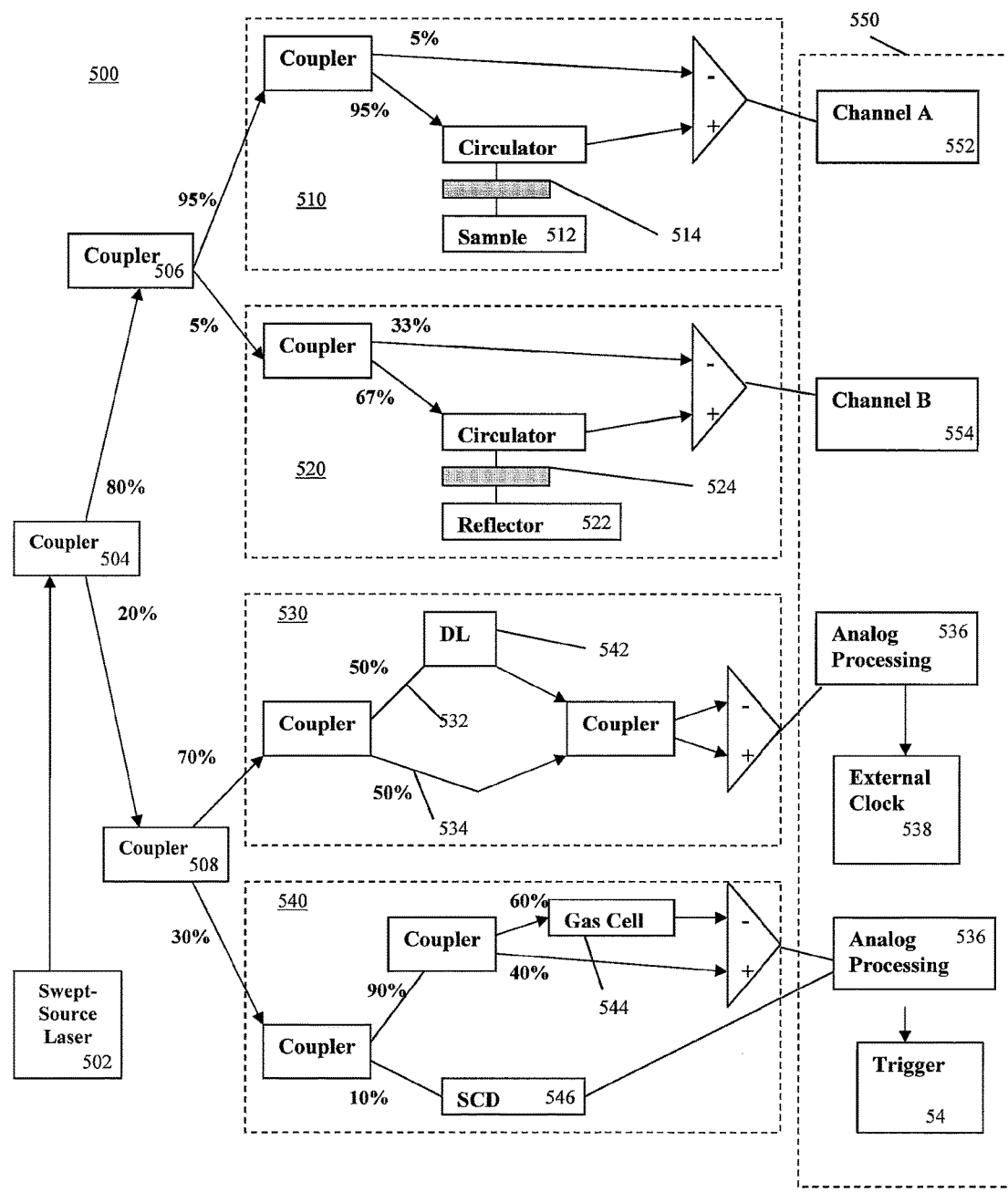
FIG. 16 is a schematic of one embodiment of the phase sensitive OCT interferometer configuration.

As shown in FIG. 16, an alternative Phase-Sensitive OCT (PS-OCT) system 500 comprising a signal interferometer 510, a reference interferometer 520, a clocking interferometer 530, a spectrally fixed trigger 540. The swept source laser 502 is coupled to an 80/20 splitter 504. The splitter 504 is coupled to a splitter 506 (95% transmittance, 5% reflection) and a splitter 508.

Light (λ=1310 nm, Δλ=100 nm, 20 KHz scan rate) emitted from a swept laser source 502 (Santec, Hackensack, N.J.) is input into four optical subsystems: the signal-interferometer 510; the reference-interferometer 520; the clocking-interferometer 530; and the spectrally fixed trigger 540. The sample under test 512 is positioned in the signal interferometer 510. Interference fringes ($F_s(v)$) are formed between light reflected from a splitter 514 and the sample 512 and directed into Channel A 552 of an analog-to-digital (A/D) converter 550 (ADC). The interference fringes ($\tau_r(v)$)

in the reference interferometer 520 are formed analogously to ($\tau_s$(v)) between light reflected from a splitter 524 and a high reflection mirror 522 and directed into Channel B 554 of the ADC 550. Interference fringes ($\tau_{c1}$(v)) in the clocking interferometer 530 are formed between light going through a first arm 532 and a second aim 534 of the Mach-Zehnder clocking interferometer 530, and after analogous bandpassing 536 served as a real time external clock 538 source for the ADC 550. The frequency of the external clock 538 depends on the optical path difference between 532 and 534 and varied with a variable Delay Line ("DL") 542. A sequence of the narrowband TTL like pulses are formed after light is outputted from a gas cell 544 (Wavelength Reference, Mulino, Oreg.) in the spectrally fixed trigger subsystem 540. The only pulse is selected using a time window produced out off a single channel detector ("SCD") 546 and serves as the spectrally fixed trigger for the ADC 550 at the AND gate using TTL pulse produced from laser sweep intensity profile.

Accuracy and sensitivity of the phase sensitive OCT instrument can be measured using a set of standardized metal films commonly used for calibrating resolution of atomic force microscopes. Sensitivity of the phase sensitive Fourier-domain OCT instrument is measured by placing a reflecting surface on a piezoelectric stepper (PolyTech PI, Auburn, Mass.) with 0.5 nm resolution. After aligning light reflection from the piezoelectric stepper, one-hundred A-scans are recorded for each position and the stepper is incremented 10 nm. Proceeding in this manner, accuracy and sensitivity of the phase sensitive Fourier-domain OCT instrument can be calibrated. Optical scanning systems that incorporate field flatteners can provide optical fields that are flat to within a fraction of a wave (e.g., 1/10 wave) a calibration procedure may be employed to correct residual phase variations that occur when scanning across the field. Calibration procedures using precision reference optical flats as reflective surfaces may be employed to correct for phase variation over the field curvature due to the scanning optics.

Figure 17A:
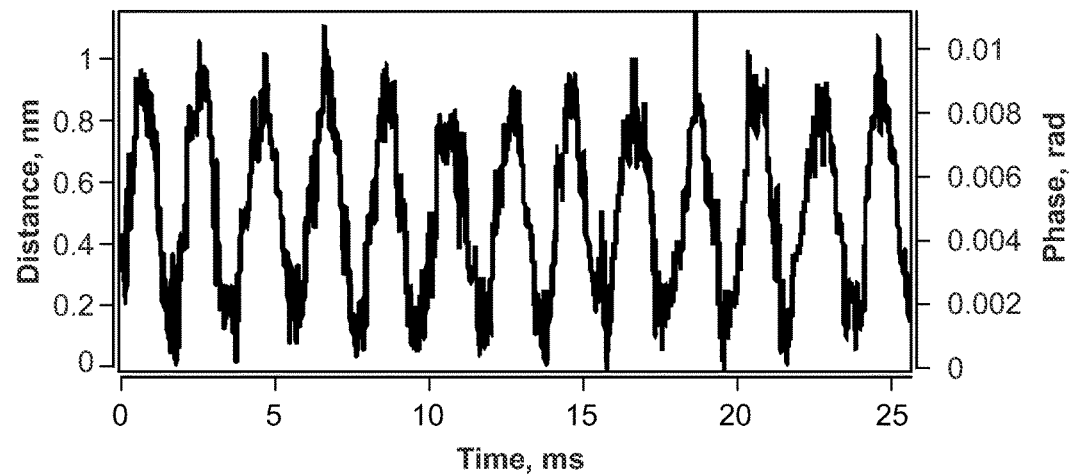
FIG. 17A-17C are graphs of the change in thickness in the piezofilm in response to application of a periodic voltage at increasing frequency (17A: 500 Hz, 17B: 1000H, 17C: 2000 Hz).
Figure 17B:
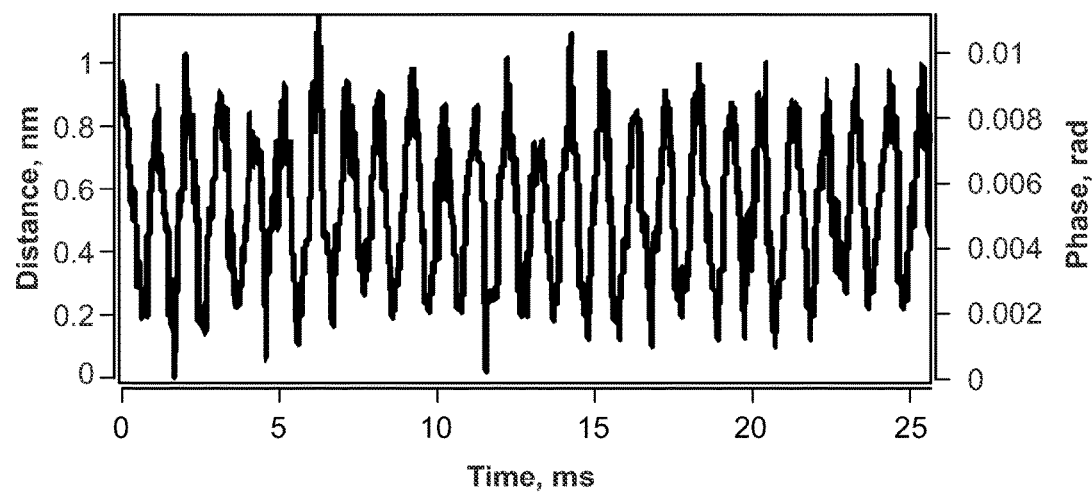
Figure 17C:
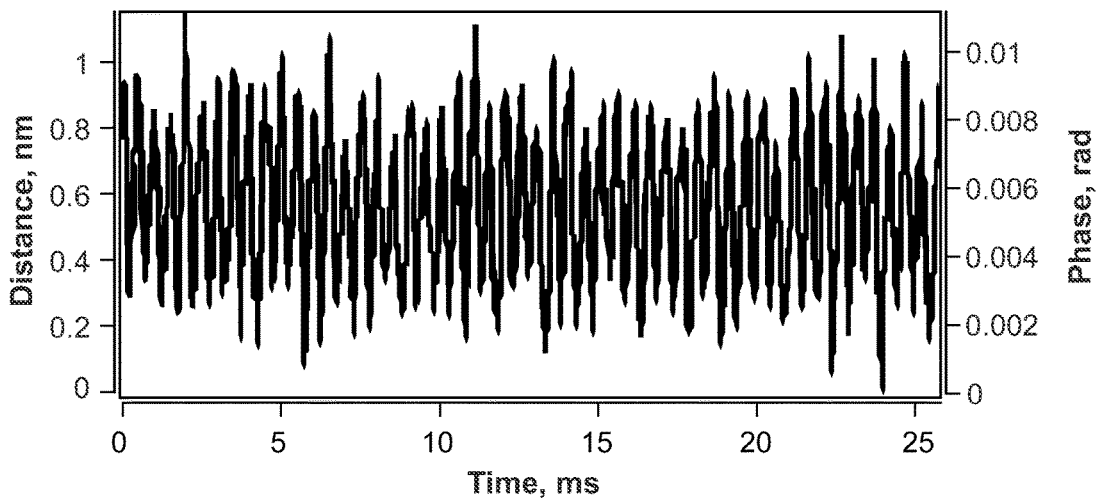

The strain constant of the PVDF copolymer piezofilm is $d_{33}$=$-38*10^{-12}$ m/V (Images SI Inc, Staten Island, N.Y.). A 10 V amplitude sinusoidal voltage to the piezofilm is applied using an Agilent function generator, which corresponds to 20 V peak peak change of voltage. The result change in the thickness of the piezofilm equals $d_{33}$*20V=0.76 nm. The voltage frequency was 500 Hz (FIG. 17A), 1000 Hz (FIG. 17B) and 2000 Hz (FIG. 17C).

The phase measurement versus time for the piezofilm induced by applied 10 V sinusoidal voltage with three different frequencies 500 Hz (17A), 1000 Hz (17B), 2000 Hz (17C). The measured phase (Y-scale on the right) is due to changing in thickness of the piezofilm. The thickness of the piezofilm (the Y-scale on the left) can be calculated from the phase measurements as T=$\Phi$*$\lambda$/(4*$\pi$), where it-measured phase (rad), $\lambda$-central wavelength of the Swept Source laser (nm).

K-Space Clock Dispersion Correction

The difference in the dispersion between the reference path and the sample path is a common problem in OCT systems. The difference in dispersion between the reference and sample path can cause a degradation of the point spread function and reduce image quality. Mathematically, the point spread function S(x) is represented by Equation (1):

$$S(x) = \int F(k(t)) e^{i\Delta\phi(k(t))} e^{jk(t)x} (dk/dt) dt + c.c., \quad (1)$$

where S(x) is point spread function of the swept source OCT system from one sharp boundary; F(k(t)) is the power spectrum of the swept source laser; Re$^{(ei\Delta\Phi(k(T)))}$=D, is the dispersion mismatch component in the arms of OCT interferometer; dk/dt=C is the component due to non-uniform clocking in k-space; k is the wavenumber; t is time; and c.c. is the complex conjugate. Dispersion D can be altered, so D*C=1.

One method addressing the degradation of the point spread function is to account for the dispersion and apply a complex resampling algorithm to the raw data acquired from the Analog to Digital Converter (ADC). Another method comprises dispersion matching of the sample path to the k-space clock path with hardware dispersion matching. The k-space clock pathway is discussed previously. A hardware based approach comprises dispersion correcting the k-space clock to include the difference in dispersion between the sample and reference path. After the difference in dispersion has been measured, it is used to modify the k-space clock. If the OCT system is being clocked by an arbitrary waveform generator, a non-dispersion correct k-space clock signal is acquired by the ADC, the non-dispersion correct k-space clock signal is modified to take into account the difference in dispersion, and then this dispersion corrected k-space clock signal is used to clock the ADC to acquire the OCT data.

Alternatively, the method comprises modifying the k-space clock optics to account for the dispersion mismatch in the sample and reference path. The k-space clock optics includes some kind of interferometer that is relying on interference. The k-space clock corrective optical elements could include a glass window, fiber optic elements, a plurality of prisms, and/or a plurality of air gaps. By modifying the optics of the k-space clock then the effect of dispersion mismatch between reference and sample paths in the interferometer may be corrected. The dispersion corrected k-space clock optics enables the OCT system to be clocked with minimal dispersion in "real time", since the k-space clock would not require non-causal resampling techniques. The real time dispersion corrected clock could also be coupled with the arbitrary waveform generator pathway, where the difference is the real time dispersion correct k-space clock does not require dispersion resampling before being used.

The dispersion characteristic D is usually smooth and cosine modulated (D=Cos [$\Delta\Phi$(k(t))]) versus k but C component can vary non-smoothly from digitized sample to digitized sample (neighbor k numbers).

The C component can vary from A-scan to A-scan. From the arbitrary waveform generator 50 (Gage CompuGen), the C component does not change from A-scan to A-scan. However, the dispersion component may still need correction from A-scan to A-scan in some embodiments of the arbitrary waveform generator.

Another approach addressing the degradation of the point spread function is the presence of an amplitude optical filter $\Phi$(k(t)) in the reference arm of interferometer, which converts Equation (1) to:

$$S(x) = \int F(k(t)) e^{i\Delta\phi(k(t))} e^{jk(t)x} (dk/dt) \Phi(k(t)) dt + c.c., \quad (2)$$

The amplitude optical filter $\Phi$(k(t)) facilitates to correct the distortion of the resolution with depth due to non-uniform k-space clocking (D*C*$\Phi$=1 may be easier to achieve than D*C=1). The depth resolution of the OCT system can be improved by effectively increasing the bandwidth of the power spectrum F(k(t)). Some power in the reference arm may be lost by damping central k-numbers and not modifying k-numbers at the edge of the spectrum.

All the Uniform Frequency Sample Clocking 10 Pathways, systems, and methods provide for external clocking of a swept laser source and can provide different Pathways, independently or in combination, to generate the clock, process the clock, and transmit the clock to the digitizer for uniform sampling of detected light in the wavenumber domain. Alternatively, all the Uniform Frequency Sample Clocking 10 Pathways may be combined with each other, in any particular combination or order. For example, an optical parameter of light can be measured by the clocking system and the optical parameter can be used in a model or look-up-table to predict the clocking wavenumber for a swept-source OCT system.

In one embodiment, the Uniform-Frequency Sample Clock Pathways for OCT systems image at least a portion of a sample. In one embodiment, the sample is a biological sample. The sample path of the OCT interferometers can be coupled to a probe or catheter via a fiber optic rotary junction to image a biological sample. The catheter can be located within a subject to allow light reflection off of subject tissues or nanoparticles to obtain optical measurements, medical diagnosis, treatment, and the like. In one embodiment, the Uniform-Frequency Sample Clock Pathways is coupled to OCT systems and catheters for imaging blood flow, such as in U.S. patent application Ser. No. 11/550,771, imaging a vessel or internal lumen of a patient, such as in U.S. patent application Ser. No. 11/446,683, and imaging nanoparticle labeled cells, such as in U.S. patent application Ser. No. 11/441,824, each herein incorporated by reference for the methods, apparatuses and systems taught therein.

Reconfiguration Between Imaging Modes

There are numerous different approaches for having a single OCT system that can switch between two different imaging modes. In one embodiment, the sweep rate and coherence length of the light source (e.g., swept source laser) is changed. That is accomplished by changing the drive waveform (and thus the sweep rate) to the optical filter responsible for instantaneous wavelength selection. For a laser, typically a slower sweep rate will inherently result in a narrower instantaneous line width and an increase in the laser's coherence length. Generally, a first imaging mode uses a high sweep rate with a relatively low coherence length (<10 mm). Such a configuration is acceptable for imaging a coronary vessel. A second imaging mode uses a lower sweep rate (<50 kHz) with a corresponding higher coherence length (>10 mm). Such a configuration is more appropriate for imaging a peripheral vessel.

The invention also contemplates reconfiguration of the sweep bandwidth over the total sweep range in order to accomplish OCT switching. Alternatively, sweeping over smaller bandwidth ranges is another way to change the sweep rate (i.e. nm/µm) and improve coherence length, but not affect the repetition rate (kHz). This could also be accomplished with changes to drive waveforms for filter and gain medium. Duty cycle would also be another parameter to reconfigure as imaging modes are switched.

Other methods include switching to a completely different filter that is designed with a different bandwidth characteristic. This switching can be performed using beam steering, MEMS, and a variety of optical switching/routing approaches. MEMS approaches involving arrays of micromirrors that can deflect an optical signal to the appropriate receiver (e.g., U.S. Pat. No. 6,396,976) may be used with methods of the invention. Piezoelectric Beam Steering involving piezoelectric ceramics provides enhanced optical switching characteristics may be used with methods of the invention. Inkjet methods involving the intersection of two waveguides so that light is deflected from one to the other when an inkjet-like bubble is created (e.g., U.S. Pat. No. 6,212,308) may be used with methods of the invention. Liquid crystals (e.g., U.S. Pat. No. 4,948,229) that rotate polarized light either 0° or 90° depending on the applied electric field to support switching may be used with methods of the invention. Thermal methods (e.g., U.S. Pat. No. 5,037,169) that vary the index of refraction in one leg of an interferometer to switch the signal on or off may be used. Nonlinear methods (e.g., U.S. Pat. No. 5,319,492) that vary the diffraction pattern in a medium by taking advantage of the material nonlinear properties to deflect light to the desired receiver may be used. Acousto-optic methods that change the refractive index as a result of strain induced by an acoustic field to deflect light (e.g., U.S. Pat. No. 6,922,498) may be used. Amplifiers and attenuators in output fibers that adjust the signal to the digital "0" power range (when the fiber is not switched to) or to the normal power range when it is (e.g., U.S. Pat. No. 7,027,211). Optical switches are further described for example in Okuno et al. (NTT Technical Review, 1(7):20-30, 2003), the content of which is incorporated by reference herein in its entirety.

In another embodiment, sampling characteristics of the OCT signal digitization are changed. OCT signal digitization is discussed above. For direct "externally" clocked digitizers, changing the sampling characteristics of the OCT signal digitization can be accomplished by changing an external K-space sample clock waveform using either optical means (e.g. switching a different wavemeter interferometer into a K-clock generator using an optical switch) or by electronic means (e.g. enabling or disabling clock multiplication circuitry). Alternatively, or "internally" (time-uniform) clocked digitizers, the sampling rate can be reconfigured directly by selection of the sampling time-base.

In other embodiments, the system is configured to work with two or more different catheters, one for each imaging mode, i.e., the different catheter types can both be used on the same reconfigurable OCT system hardware. For example, it is expected that a different catheter could be used for coronary versus peripheral imaging. In this embodiment, the OCT system includes a connector equipped with an RFID reader than can operably couple to an RFID component on a catheter. The reader on the system obtains information from the catheter and determines whether a coronary imaging catheter or a peripheral imaging catheter is connected to the system and switches to the appropriate layout. RFID sensors and their use are described for example in Broughton et al. (U.S. patent application number 2003/0050871), Kalantar (U.S. Pat. No. 6,954,737), and Kates (U.S. patent application number 2006/0267756).

In another embodiment, the system includes two image acquisition modules. Reconfiguration in this embodiment is accomplished by changing the software that processes and handles the image acquisition. That can be accomplished by running a different software program in each of the operational modes, or by changing parameters of the software to handle image streams with different imaging rates and field of views. It can also be accomplished by re-programming an embedded processor responsible for image processing.

In another embodiment, changing the software which provides a Graphical User Interface is used to switch between the two imaging modes. It is expected that different user features may be needed for coronary imaging versus peripheral imaging.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A reconfigurable optical coherence tomography (OCT) system configured to reconfigure between at least a first imaging mode optimized for coronary imaging and a second imaging mode optimized for peripheral imaging, the system comprising:
   a reconfigurable swept-source laser configured to be adjusted between a first setting corresponding to the first imaging mode and a second setting corresponding to the second imaging mode, wherein the reconfigurable swept-source laser comprises:
      a first filter comprising a first bandwidth characteristic corresponding to the first imaging mode;
      a second filter comprising a second bandwidth characteristic corresponding to the second imaging mode; and
      an optical switch configured to switch an optical signal between the first filter and the second filter;
   wherein, in the first setting, the swept-source laser has a first sweep rate with a first coherence length and the first imaging mode is for imaging a coronary vessel; and
   wherein, in the second setting, the swept-source laser has a second sweep rate with a second coherence length, the second sweep rate being less than the first sweep rate and the second coherence length being greater than the first coherence length, and the second imaging mode is for imaging a peripheral vessel;
   wherein sampling characteristics of OCT signal digitization are changed between the first and second imaging modes by changing an external K-space sample clock waveform by switching a different wavemeter interferometer into a K-clock generator for each of the imaging modes.

2. The system according to claim 1, wherein the OCT system comprises two different software image acquisition modules, one for each imaging mode.

3. The system according to claim 1, wherein the system is compatible with two different catheters, one for each imaging mode.

4. The system according to claim 1, further comprising an apparatus selected from the group consisting of: a spectroscopic apparatus, an intravascular ultrasound (IVUS) apparatus, a Forward-Looking IVUS (FLIVUS) apparatus, a high intensity focused ultrasound (HIFU) apparatus, a radiofrequency apparatus, a thermal imaging or thermography apparatus, an optical light-based imaging apparatus, a magnetic resonance imaging (MRI) apparatus, a radiography apparatus, a nuclear imaging apparatus, a photoacoustic imaging apparatus, an electrical impedance tomography apparatus, an elastography apparatus, an intracardiac echocardiography (ICE) apparatus, a forward looking ICE apparatus, an orthopedic apparatus, a spinal imaging apparatus, and a neurological imaging apparatus.

5. The system according to claim 1, wherein the optical switch comprises a piezoelectric beam steering optical switch.

6. The system according to claim 1, wherein the optical switch comprises a MEMS-type optical switch.

* * * * *